US012612659B2

(12) United States Patent
Otto et al.

(10) Patent No.: US 12,612,659 B2
(45) Date of Patent: Apr. 28, 2026

(54) DEVICES INCLUDING PARTICLES COUPLED TO ELECTRODES, AND METHODS OF MAKING AND USING THE SAME

(71) Applicant: Illumina, Inc., San Diego, CA (US)

(72) Inventors: Rico Otto, San Diego, CA (US); Hayden Black, San Diego, CA (US); Jeffrey Mandell, Rancho Santa Fe, CA (US)

(73) Assignee: ILLUMINA, INC., San Diego, CA (US)

( * ) Notice: Subject to any disclaimer, the term of this patent is extended or adjusted under 35 U.S.C. 154(b) by 621 days.

(21) Appl. No.: 17/921,941

(22) PCT Filed: May 6, 2021

(86) PCT No.: PCT/US2021/031171
§ 371 (c)(1),
(2) Date: Oct. 27, 2022

(87) PCT Pub. No.: WO2021/231184
PCT Pub. Date: Nov. 18, 2021

(65) Prior Publication Data
US 2023/0175055 A1     Jun. 8, 2023

Related U.S. Application Data

(60) Provisional application No. 63/023,001, filed on May 11, 2020, provisional application No. 63/022,990, filed on May 11, 2020.

(51) Int. Cl.
*C12Q 1/6869*     (2018.01)
(52) U.S. Cl.
CPC .................................. *C12Q 1/6869* (2013.01)

(58) Field of Classification Search
CPC ..... H01M 2008/1293; H01M 2250/20; H01M 8/04022; H01M 8/04268; H01M 8/04302;
(Continued)

(56) References Cited

U.S. PATENT DOCUMENTS

| | | |
|---|---|---|
| 6,685,812 B2 | 2/2004 | Miles |
| 7,074,569 B2 | 7/2006 | Woo |

(Continued)

FOREIGN PATENT DOCUMENTS

| | | |
|---|---|---|
| CN | 102384934 A | 3/2012 |
| CN | 106591103 B | 6/2021 |

(Continued)

OTHER PUBLICATIONS

Ah et al., "Electric detection of DNA hybridization by nanoparticle nanoswitch," Current Applied Physics 6(S1):e157-e160 (Aug. 2006).
(Continued)

*Primary Examiner* — Jennifer Wecker
*Assistant Examiner* — Jonathan Bortoli
(74) *Attorney, Agent, or Firm* — Sheppard, Mullin, Richter & Hampton LLP; Jaime D. Choi

(57)     ABSTRACT

In some examples, a device includes first and second electrodes separated from one another by a space; a particle coupled to the first electrode via a first plurality of bonds, and coupled to the second electrode via a second plurality of bonds; and a polymerase coupled to the particle. In some examples, a composition includes first and second electrodes separated from one another by a space; a fluid including a first electrically conductive label having a length at least as long as a length of the space; and detection circuitry to generate a first signal responsive to transient formation, using the first electrically conductive label, of a first electrically conductive bridge between the first and second electrodes.

23 Claims, 18 Drawing Sheets

(58) Field of Classification Search
CPC ........... H01M 8/04335; H01M 8/0435; H01M
8/04373; H01M 8/04708; H01M 8/04716;
H01M 8/04738; H01M 8/0618; Y02E
60/50; Y02T 90/40; C12Q 1/6869; C12Q
2535/122; C12Q 2563/149; C12Q
2565/607
See application file for complete search history.

(56)                    References Cited

U.S. PATENT DOCUMENTS

| | | | |
|---|---|---|---|
| 7,176,482 | B1 | 2/2007 | Ben-Jacob et al. |
| 7,556,923 | B1 | 7/2009 | Hedgpeth |
| 10,036,064 | B2 | 7/2018 | Merriman et al. |
| 10,093,975 | B2 | 10/2018 | Esfandyarpour |
| 2002/0072054 | A1 | 6/2002 | Miles et al. |
| 2003/0203394 | A1 | 10/2003 | Eichen et al. |
| 2004/0146863 | A1 | 7/2004 | Pisharody et al. |
| 2004/0209355 | A1 | 10/2004 | Edman et al. |
| 2006/0146323 | A1 | 7/2006 | Bratkovski et al. |
| 2006/0246497 | A1 | 11/2006 | Huang et al. |
| 2010/0101956 | A1 | 4/2010 | Choi et al. |
| 2010/0184062 | A1 | 7/2010 | Steinmueller-Nethl et al. |
| 2013/0303404 | A1 | 11/2013 | Connolly |
| 2013/0310548 | A1 | 11/2013 | Park |
| 2016/0376310 | A1 | 12/2016 | Binder et al. |
| 2017/0044605 | A1* | 2/2017 | Merriman .......... G01N 27/3272 |
| 2017/0240962 | A1 | 8/2017 | Merriman et al. |
| 2018/0155773 | A1 | 6/2018 | Gunderson et al. |
| 2018/0155774 | A1 | 6/2018 | Gunderson et al. |
| 2018/0305727 | A1* | 10/2018 | Merriman .............. C12Q 1/485 |
| 2019/0041378 | A1 | 2/2019 | Choi et al. |
| 2019/0094175 | A1* | 3/2019 | Merriman .......... G01N 27/3278 |

FOREIGN PATENT DOCUMENTS

| | | | |
|---|---|---|---|
| EP | 3587591 | A1 | 1/2020 |
| KR | 101220869 | B1 | 1/2013 |
| RU | 2532855 | C2 | 11/2014 |
| TW | 200637916 | A | 11/2006 |
| WO | 2000/060125 | A2 | 10/2000 |
| WO | 2009/003208 | A1 | 1/2009 |
| WO | 2010/132727 | A1 | 11/2010 |
| WO | 2016196755 | A1 | 8/2016 |
| WO | 2017/189930 | A1 | 11/2017 |
| WO | 2018/026855 | A1 | 2/2018 |
| WO | 2020/005557 | A1 | 1/2020 |
| WO | 2021/225953 | A1 | 11/2021 |

OTHER PUBLICATIONS

Dachlika et al., "Formation of Dimers Composed of a Single Short dsDNA Connecting Two Gold Nanoparticles," Journal of Self-Assembly and Molecular Electronics 1:85-99 (2012).
Danckwerts et al., "Optical frequency mixing at coupled gold nanoparticles," Phys. Rev. Lett. 98:026104 (2007).
Díez-Pérez et al., "Rectification and stability of a single molecular diode with controlled orientation," Nature Chemistry 1:635-641 (2009).
Díez-Pérez et al., "Rectification and stability of a single molecular diode with controlled orientation," Nature Chemistry 1:635-641 (2009). Supplementary Information.
Huang et al., "Single Molecule Junctions Formed via Au-Thiol Contact: Stability and Breakdown Mechanism," J. Am. Chem. Soc. 129(43):13225-13231 (2007).
Hughes et al., "Dielectrophoretic trapping of single sub-micrometre scale bioparticles," J. Phys. D: Appl. Phys. 31:2205-2210 (1998).
International Search Report and Written Opinion for PCT/US2021/031171 dated Sep. 17, 2021; 14 pages.
Kretschmer et al., "Pearl Chain Formation by Nanoparticles in Microelectrode Gaps by Dielectrophoresis," Langmuir 20:11797-11801 (2004).

Li et al., "Electric Field Breakdown in Single Molecule Junctions," J. Am. Chem. Soc. 137(15):5028-5033 (2015).
Li et al., "Electric Field Breakdown in Single Molecule Junctions," J. Am. Chem. Soc. 137:5028-5033 (2015) Supporting Information.
Lu et al., "Blowing the Fuse: Berry's Phase and Runaway Vibrations in Molecular Conductors," Nano Letters 10:1657-1663 (2010).
Paolitto; "The origami of life," Oxford News Blog (Aug. 25, 2015).
Ramakrishnan et al., "Structural stability of DNA origami nanostructures under application-specific conditions," Computational and Structural Biotechnology Journal 16:342-349 (2018).
Schulze et al., "Resonant electron heating and molecular phonon cooling in single C60 junctions," arXiv:0803.1358 [cond-mat.mtrl-sci]; (Feb. 21, 2013).
Shen et al., "Dielectrophoretic trapping of multilayer DNA origami nanostructures and DNA origami-induced local destruction of silicon dioxide," Electrophoresis 36(2):255-262 (2015).
Shen et al., "Plasmonic nanostructures through DNA-assisted lithography," Science Advances 4(2) (Feb. 2, 2018).
Wang et al., "The Beauty and Utility of DNA Origami," Chem 2:359-382 (2017).
Zheng et al., "Towards Single Molecule Manipulation with Dielectrophoresis Using Nanoelectrodes," 3rd IEEE International Conference on Nanotechnology (NANO); (Sep. 2003).
Artés, J.M., et al.; "Conformational gating of DNA conductance"; Nature Communications; 6:8870; Dec. 9, 2015.
Bhaduri, S.; et al.: "An overview of recent advances in duplex DNA recognition by small molecules" Beilstein Journal of Organic Chemistry 14:1051-1086 (2018).
Boyle, A. L.: "Applications of de novo designed peptides" in Peptide Applications in Biomedicine, Biotechnology and Bioengineering 51-86 (Woodhead Publishing 2018).
Buzzeo et al.; "Redmond Red as a Redox Probe for the DNA-Mediated Detection of Abasic Sites", Bioconjugate Chemistry 19(11):2110-2112 (2008).
Creasey, R. C. G.; et al.: "Biomimetic Peptide Nanowires Designed for Conductivity" ACS Omega 4:1748-1756 (2019).
Creasey, R. C. G.; et al.: "Improved electrical conductance through self-assembly of bioinspired peptides into nanoscale fibers" Materials Chemistry and Physics 158:52-59 (2015).
Eckert, D. M.; et al.: "Design of potent inhibitors of HIV-1 entry from the gp41 N-peptide region" Proceedings of the National Academy of Sciences of the United States of America 98(20):11187-11192 (2001).
Guo, C.; et al.: "Tuning electronic transport via hepta-alanine peptides junction by tryptophan doping" Proceedings of the National Academy of Sciences of the United States of America 113(39):10785-10790 (2016).
Harashima, T.; et al.: "Single-molecule conductance of DNA gated and ungated by DNA-binding molecules" Chemical Communications 53:10378-10381 (2017).
Hölzel, R., et al.; "Oriented and vectorial immobilization of linear M13 dsDNA between interdigitated electrodes—towards single molecule DNA nanostructures"; Biosensor and Bioelectronics; 2003; 18:555-564; (Year: 2003).
Ing, N. L.; et al.: "Electronic Conductivity in Biomimetic a-Helical Peptide Nanofibers and Gels" ACS Nano 12:2652-2661 (2018).
Ing, N. L.; et al.: "Going the Distance: Long-Range Conductivity in Protein and Peptide Bioelectronic Materials" Journal of Physical Chemistry B 122:10403-10423 (2018).
Kai, M.; et al.: "Distance dependence of long-range electron transfer through helical peptides" Journal of Peptide Science 14:192-202 (2008).
Kim, Y.; et al.: "A peptide with alternating lysines can act as a highly specific Z-DNA binding domain" Nucleic Acids Research 34(17):4937-4942 (2006).
Kondo, J.; et al.: "A metallo-DNA nanowire with uninterrupted one-dimensional silver array" Nature Chemistry 9:956-960 (2017).
Kubo, T.; et al.: "Structure and affinity of DNA binding peptides" Nucleic Acids Symposium Series 44:49-50 (2000).
Liu, B. A.; et al.: "High-throughput analysis of peptide binding modules" Proteomics 12(10):1527-1546 (2012).
Loakes, "The applications of universal DNA base analogues", Nucleic Acids Research 29(12): 2437-2447 (2001).

(56)                    References Cited

OTHER PUBLICATIONS

Luscombe, N. M.; et al.: "An overview of the structures of protein-DNA complexes" Genome Biology 1(1):reviews001.1-001.37 (2000).

Matic, J.; et al.: "Advances in Peptide-based DNA/RNA-Intercalators" Current Protein & Peptide Science 17(2):127-134 (2016).

Okyay, A. K.; et al.: "Using nanogap in label-free impedance based electrical biosensors to overcome electrical double layer effect" Microsystem Technologies 23:889-897 (2017).

Reguera, G.; et al.: "Extracellular electron transfer via microbial nanowires" Nature 435:1098-1101 (2005).

Reverdatto, S.; et al.: "Peptide Aptamers: Development and Applications" Current Topics in Medicinal Chemistry 15(12):1082-1101 (2015).

Shah, A.; et al.: "Electron transfer in peptides" Chemical Society Reviews 44:1015-1027 (2015).

Shimizu, M.; et al.: "Oligo(2'-O-methyl)ribonucleotides. Effective probes for duplex DNA" Federation of European Biochemical Societies 302(2):155-158 (1992).

Sorensen, J. J.; et al.: "Solution structure of a dsDNA:LNA triplex" Nucleic Acids Research 32(20):6078-6085 (2004).

Thomas, F.; et al.: "A Set of de Novo Designed Parallel Heterodimeric Coiled Coils with Quantified Dissociation Constants in the Micromolar to Sub-nanomolar Regime" Journal of the American Chemical Society 135:5161-5166 (2013).

Travers, A.: "DNA-Binding Proteins" Encyclopedia of Genetics 541-544 (2001).

Walshaw, J.; et al.: "Extended knobs-into-holes packing in classical and complex coiled-coil assemblies" Journal of Structural Biology 144:349-361 (2003).

Woolfson, D. N.; et al.: "New currency for old rope: from coiled-coil assemblies to $\alpha$-helical barrels" Current Opinion in Structural Biology 22:432-441 (2012).

Xiang, L., et al.; "Gate-controlled conductance switching in DNA"; Nature Communications; 8:14471; Feb. 20, 2017.

Xiong, K., et al.; "Sliding on DNA: from peptides to small molecules"; Angew Chem Int Ed Engl.; 55:48; 15110-15114; Nov. 21, 2016.

Xu, W.; et al.: "Anti-peptide aptamers recognize amino acid sequence and bind a protein epitope." Proceedings of the National Academy of Sciences of the United States of America 93(15):7475-7480 (1996).

Zhang, Z.; et al.: "Selection and application of peptide-binding peptides" Nature Biotechnology 18:71-74 (2000).

Zhou, Z.; et al.: "DNA-RNA triple helix formation can function as a cis-acting regulatory mechanism at the human $\beta$-globin locus" Proceedings of the National Academy of Sciences of the United States of America 116(13):6130-6139 (2019).

* cited by examiner

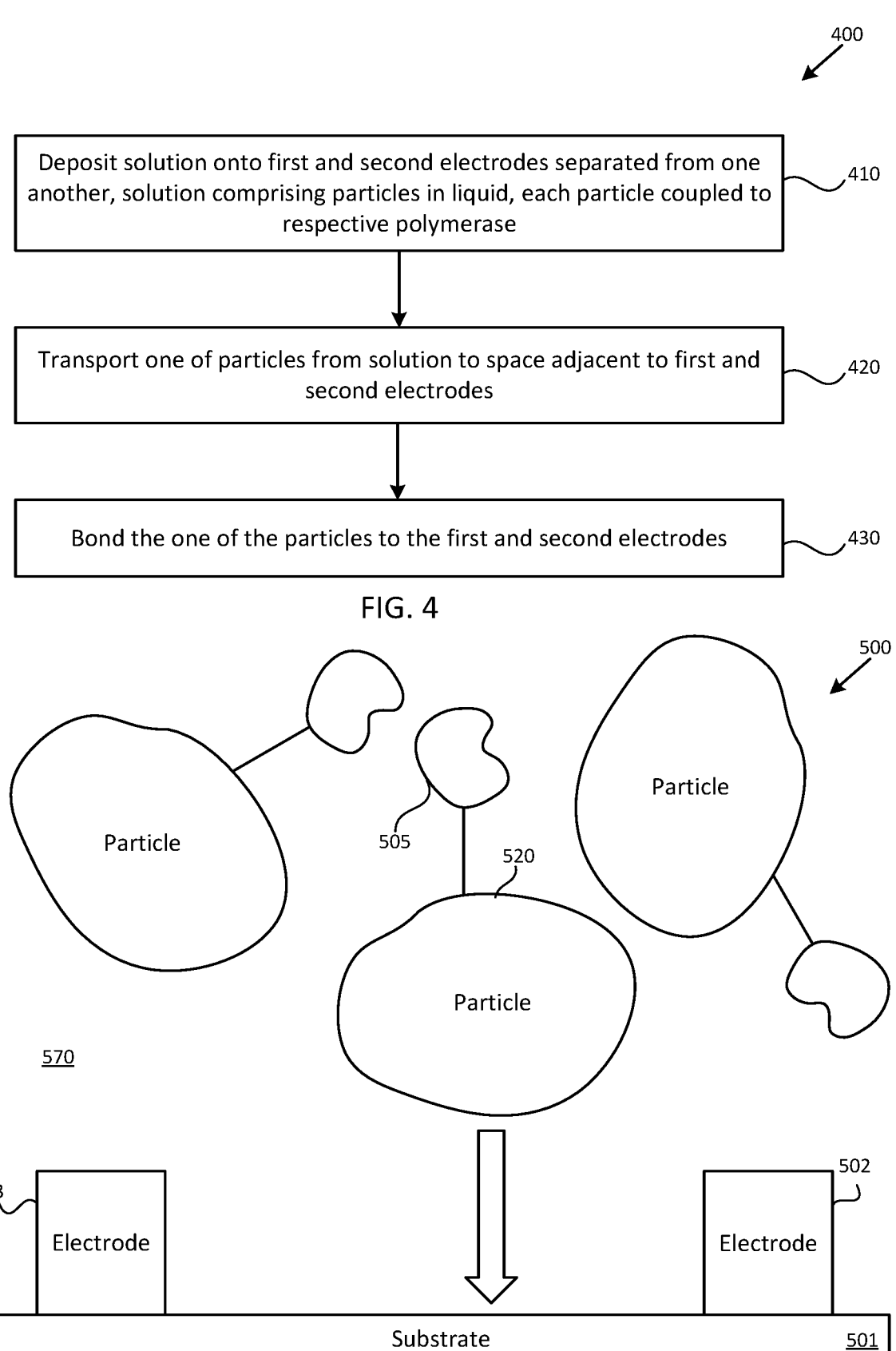

400

Deposit solution onto first and second electrodes separated from one another, solution comprising particles in liquid, each particle coupled to respective polymerase — 410

Transport one of particles from solution to space adjacent to first and second electrodes — 420

Bond the one of the particles to the first and second electrodes — 430

Particle

Particle

Particle

505

520

570

503 — Electrode

502 — Electrode

Substrate          501

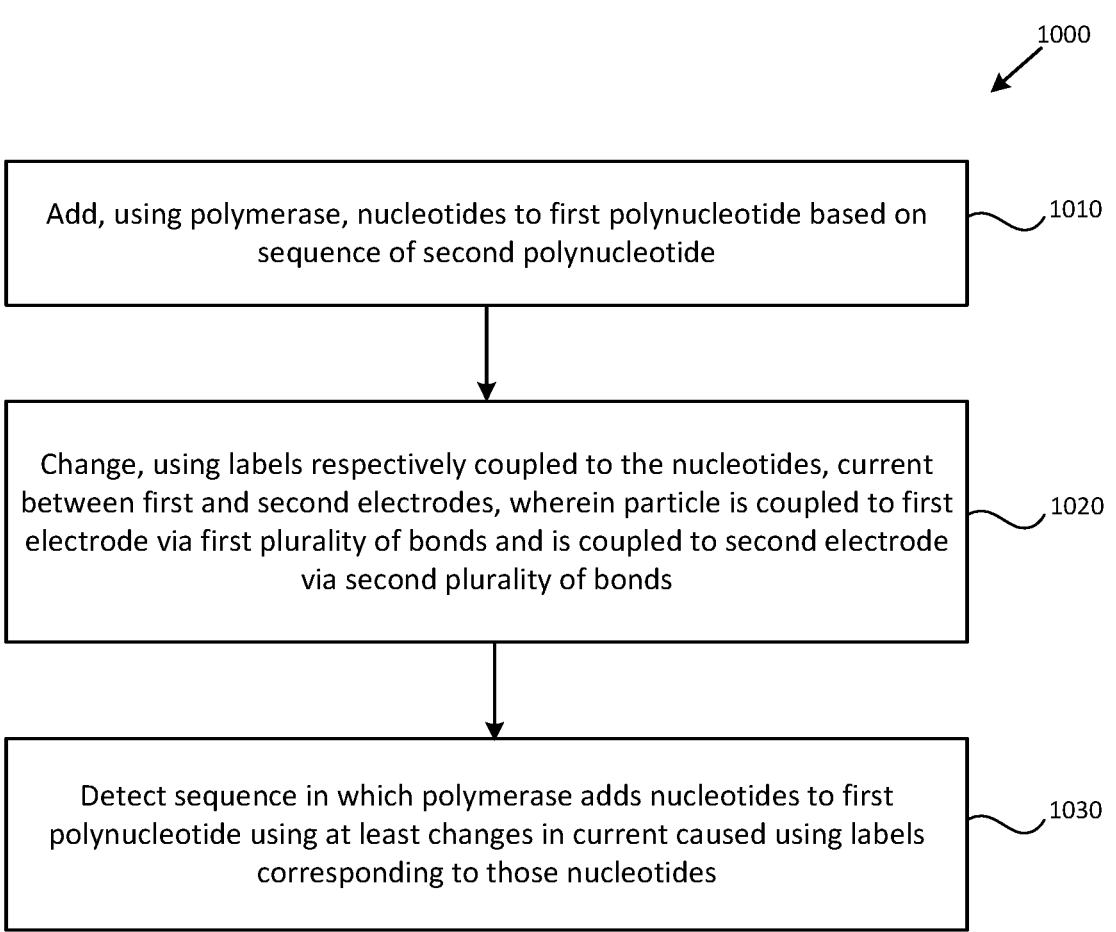

1000

Add, using polymerase, nucleotides to first polynucleotide based on sequence of second polynucleotide

1010

Change, using labels respectively coupled to the nucleotides, current between first and second electrodes, wherein particle is coupled to first electrode via first plurality of bonds and is coupled to second electrode via second plurality of bonds

1020

Detect sequence in which polymerase adds nucleotides to first polynucleotide using at least changes in current caused using labels corresponding to those nucleotides

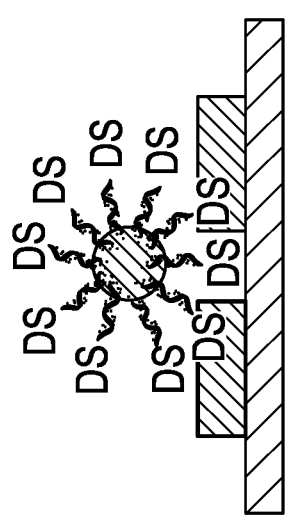
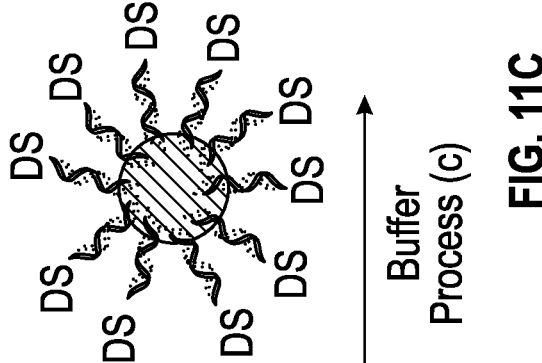
Buffer Process (c)
FIG. 11C
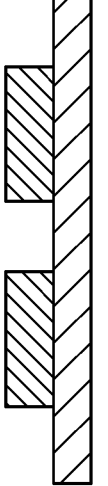

5' - Thiol Oligo

Buffer Process (a)

Buffer Process (b)

DEVICES INCLUDING PARTICLES COUPLED TO ELECTRODES, AND METHODS OF MAKING AND USING THE SAME

CROSS-REFERENCE TO RELATED APPLICATIONS

This application is a national stage application under 35 U.S.C. § 371 of International Patent Application No. PCT/US2021/031171, filed on May 6, 2021, entitled "Devices Including Particles Coupled to Electrodes, and Methods of Making and Using the Same," the entire contents of which are incorporated by reference herein, and which claims the benefit of the following applications, the entire contents of each of which are incorporated by reference herein:

U.S. Provisional Patent Application No. 63/022,990, filed May 11, 2020 and entitled "Devices Including Particles Coupled to Electrodes, and Methods of Making and Using the Same;" and U.S. Provisional Patent Application No. 63/023,001, filed May 11, 2020 and entitled "Compositions Including Labels That Transiently Form or Selectively Complete Bridges Between Electrodes."

BACKGROUND

A significant amount of academic and corporate time and energy has been invested into sequencing polynucleotides, such as DNA. Some sequencing systems use "sequencing by synthesis" (SBS) technology and fluorescence-based detection. However, fluorescence-based detection may require optical components such as excitation light sources, imaging devices, and the like, which may be complex, time-consuming to operate, and costly. Furthermore, many sequencing strategies, are limited to short reads of ensemble clusters of DNA segments. Technologies that enable long reads of single DNA molecules are of great importance for improving overall accuracy of sequencing.

SUMMARY

Devices including particle-based bridges between electrodes are provided herein. Methods of making such devices, and compositions and methods using such devices for electronically sequencing polynucleotides via distinct electrical signals of each base (A, T, C, or G) are disclosed. A device may include first and second electrodes separated from one another by a space, a particle, and a polymerase. The particle may be coupled to the first electrode via a plurality of bonds, and coupled to the second electrode via a plurality of bonds. The polymerase may be coupled to the particle.

Provided in some examples herein is a device that includes first and second electrodes separated from one another by a space. The device includes a particle coupled to the first electrode via a plurality of bonds, and coupled to the second electrode via a plurality of bonds. The device includes a polymerase coupled to the particle.

In some examples, the particle forms at least part of an electrically conductive bridge between the first and second electrodes.

In some examples, the particle is electrically nonconductive.

In some examples, the particle includes a polymer having a tertiary structure. In some examples, the polymer having the tertiary structure includes a polynucleotide or a polypeptide. In some examples, the polynucleotide or polypeptide is folded and cross-linked into a tertiary structure having a central constriction. The central constriction may form part of an electrically conductive bridge between the first and second electrodes.

In some examples, the particle includes a nanoparticle with functional groups bonding the nanoparticle to the first and second electrodes. In some examples, the nanoparticle is inorganic.

Additionally, or alternatively, the particle in some examples has a diameter of at least about 10% of a length of the space.

Additionally, or alternatively, the particle in some examples includes a pair of nanoparticles coupled to one another by a linker.

Provided in some examples herein is a method of making a device. The method includes depositing a solution onto first and second electrodes separated from one another. The solution includes particles in a liquid, each particle coupled to a respective polymerase. The method includes transporting one of the particles from the solution to a space adjacent to the first and second electrodes. The method includes bonding the one of the particles to each of the first and second electrodes.

In some examples, the transporting includes dielectrophoretically or magnetically trapping the one of the particles at the first and second electrodes.

Additionally, or alternatively, the bonding in some examples includes forming a first plurality of bonds between the first electrode and the one of the particles, and forming a second plurality of bonds between the second electrode and the one of the particles.

Additionally, or alternatively, the method in some examples further includes sterically excluding, using the one of the particles, other particles from the space adjacent to the first and second electrodes.

In some examples, the particle forms at least part of an electrically conductive bridge between the first and second electrodes.

In some examples, the particle is electrically nonconductive.

In some examples, the particle includes a polymer having a tertiary structure. In some examples, the polymer having the tertiary structure includes a polynucleotide or a polypeptide. In some examples, the polynucleotide or polypeptide is folded and cross-linked into a tertiary structure having a central constriction, the central constriction forming part of an electrically conductive bridge between the first and second electrodes.

In some examples, the particle includes a nanoparticle with functional groups bonding the nanoparticle to the first and second electrodes. In some examples, the nanoparticle is inorganic.

Additionally, or alternatively, the particle in some examples has a diameter of at least about 10% of a length of the space.

Provided in some examples herein is a device array that includes a solid substrate, and a plurality of electrode pairs disposed on the solid substrate. The electrodes of each electrode pair are separated from one another by a respective space. The device array includes a plurality of particles, each bonded to the electrodes of a respective electrode pair. A majority of the electrode pairs respectively are bonded to a single one of the particles. The device array includes a plurality of polymerases, each polymerase being coupled to a respective one of the particles.

In some examples, the respective spaces vary amongst the electrode pairs to which the particles are respectively bonded.

Provided in some examples herein is a method of making a device array that includes depositing a solution onto a solid substrate having a plurality of electrode pairs disposed thereon. The electrodes of each electrode pair are separated from one another by a respective space. The solution includes particles in a liquid. Each particle is coupled to a respective polymerase. The method includes transporting the particles from the solution to respective ones of the spaces, and bonding one of the particles to the electrodes of each electrode pair. A majority of the electrode pairs respectively are bonded to exactly one of the particles.

In some examples, the transporting includes dielectrophoretically or magnetically trapping the one of the particles at the electrodes of the respective one of the electrode pairs.

Additionally, or alternatively, the bonding in some examples includes forming a plurality of bonds between the one of the particles and each of the electrodes of the respective one of the electrode pairs.

Additionally, or alternatively, the method in some examples further includes sterically excluding, using the one of the particles, any other particles from contacting the electrodes of the respective one of the electrode pairs.

Provided in some examples herein is a composition that includes first and second electrodes separated from one another by a space. The composition includes a particle coupled to the first electrode via a plurality of bonds, and coupled to the second electrode via a plurality of bonds. The composition includes first and second polynucleotides. The composition includes a plurality of nucleotides, each nucleotide being coupled to a corresponding label. The composition includes a polymerase coupled to the particle and to add the nucleotides to the first polynucleotide using at least a sequence of the second polynucleotide. The composition includes detection circuitry to detect a sequence of the addition of the nucleotides to the first polynucleotide using at least changes in a current between the first and second electrodes. The changes are responsive to the labels corresponding to those nucleotides.

In some examples, the particle forms at least part of an electrically conductive bridge between the first and second electrodes, and the labels alter the current between the first and second electrodes through the bridge.

In some examples, the particle is electrically nonconductive, and the labels respectively form transient electrically conductive bridges between the first and second electrodes via which the current flows.

In some examples, the particle includes a polymer having a tertiary structure. As a further option, the polymer having the tertiary structure includes DNA or a polypeptide.

Additionally, or alternatively, the tertiary structure forms an electrically conductive bridge between the first and second electrodes, and wherein the labels alter the current between the first and second electrodes by hybridizing to the electrically conductive bridge.

In some examples, the particle includes a nanoparticle with functional groups bonding the nanoparticle to the first and second electrodes.

In some examples, the nanoparticle is electrically nonconductive. The labels respectively may form transient electrically conductive bridges between the first and second electrodes via which the current flows. In some examples, at least one of the labels is selected from the group consisting of carbon dots, electrically conductive polymers, pi-conjugated small molecules, nanotubes, and fullerenes. Additionally, or alternatively, the nanoparticle and the functional groups in some examples form at least part of an electrically conductive bridge between the first and second electrodes. The labels alter the current between the first and second electrodes by hybridizing to the functional groups.

In some examples, the particle includes a pair of nanoparticles coupled to one another by a linker. The labels alter the current between the first and second electrodes by hybridizing to the linker.

Provided in some examples herein is a method for sequencing a polynucleotide. The method includes adding, using a polymerase, nucleotides to a first polynucleotide using at least a sequence of a second polynucleotide. The method includes changing, using labels respectively coupled to the nucleotides, a current between first and second electrodes. A particle is coupled to the first electrode via a plurality of bonds and is coupled to the second electrode via a plurality of bonds. The method includes detecting a sequence in which the polymerase adds the nucleotides to the first polynucleotide using at least changes in the current that are caused using the labels corresponding to those nucleotides.

In some examples, the particle forms at least part of an electrically conductive bridge between the first and second electrodes, and the labels alter the current between the first and second electrodes through the bridge.

In some examples, the particle is electrically nonconductive, and the labels respectively form transient electrically conductive bridges between the first and second electrodes via which the current flows.

In some examples, the particle includes a polymer having a tertiary structure. In some examples, the polymer having the tertiary structure includes DNA or a polypeptide.

Additionally, or alternatively, the tertiary structure forms an electrically conductive bridge between the first and second electrodes. The labels alter the current between the first and second electrodes by hybridizing to the electrically conductive bridge.

In some examples, the particle includes a nanoparticle with functional groups bonding the nanoparticle to the first and second electrodes. In some examples, the nanoparticle is electrically nonconductive. The labels respectively form transient electrically conductive bridges between the first and second electrodes via which the current flows. In some examples, at least one of the labels is selected from the group consisting of carbon dots, electrically conductive polymers, pi-conjugated small molecules, nanotubes, and fullerenes. Additionally, or alternatively, in some examples the nanoparticle and the functional groups form at least part of an electrically conductive bridge between the first and second electrodes. The labels alter the current between the first and second electrodes by hybridizing to the functional groups.

In some examples, the particle includes a pair of nanoparticles coupled to one another by a linker, and wherein the labels alter the current between the first and second electrodes by hybridizing to the linker.

Devices including bridges between electrodes also are provided herein. Methods of making such devices, and compositions and methods using such devices for electronically sequencing polynucleotides via distinct electrical signals of each base (A, T, C, or G) are disclosed. A device may include first and second electrodes separated from one another by a space, and a polymerase. A bridge between the first and second electrodes may be completed, or may be transiently formed, using labels.

Provided in some examples herein is a composition including first and second electrodes separated from one another by a space. The composition includes a fluid including a first electrically conductive label having a length at least as long as a length of the space. The composition includes detection circuitry to generate a first signal responsive to transient formation, using the first electrically conductive label, of a first electrically conductive bridge between the first and second electrodes.

In some examples, the first electrically conductive label includes a carbon dot, electrically conductive polymer, pi-conjugated small molecule, nanotube, or fullerene.

Additionally, or alternatively, in some examples the fluid further includes a second electrically conductive label having a length at least as long as a length of the space. The detection circuitry is to generate a second signal responsive to transient formation, using the second electrically conductive label, of a second electrically conductive bridge between the first and second electrodes. In some examples, the detection circuitry further is to distinguish between formation of the first electrically conductive bridge and the second electrically conductive bridge using at least a difference between the first signal and the second signal.

In some examples, the first electrically conductive label transiently bonds to each of the first and second electrodes to form the first electrically conductive bridge. In some examples, the first electrically conductive label includes a first reactive group to transiently bond to the first electrode, and a second reactive group to transiently bond to the second electrode. In some examples, the first and second reactive groups are selected from the group consisting of: amines, isothiocyanides, phosphines, carboxyls, selenos, pyridines, and methylsulfides. Additionally, or alternatively, the detection circuitry in some examples further is to apply a bias voltage across the first electrically conductive bridge that disrupts the transient bond between the first reactive group and the first electrode or the transient bond between the second reactive group and the second electrode. In some examples, the bias voltage disrupts the transient bond between the first reactive group and the first electrode and the transient bond between the second reactive group and the second electrode.

In some examples, the composition further includes a polymerase coupled adjacent to the first and second electrodes, and a nucleotide coupled to the first electrically conductive label. The first electrically conductive label forms the first electrically conductive bridge responsive to action, using the polymerase, on the nucleotide. In some examples, the composition includes a particle coupled to the first and second electrodes and to the polymerase. In some examples, the particle is electrically nonconductive.

Provided in some examples herein is a method for sequencing. The method includes adding, using a polymerase, nucleotides to a first polynucleotide using at least a sequence of a second polynucleotide. The method includes transiently forming, using electrically conductive labels respectively coupled to the nucleotides, electrically conductive bridges between first and second electrodes. The method includes detecting a sequence in which the polymerase adds the nucleotides to the first polynucleotide using at least the transient formation of the electrically conductive bridges. In some examples, the electrically conductive labels independently include one or more of a carbon dot, electrically conductive polymer, pi-conjugated small molecule, nanotube, or fullerene. Additionally, or alternatively, in some examples the sequence is detected using at least differences in electrical conductivities across the electrically conductive bridges.

In some examples, the electrically conductive labels transiently bond to each of the first and second electrodes to form the electrically conductive bridges. In some examples, each electrically conductive label includes a first reactive group to transiently bond to the first electrode, and a second reactive group to transiently bond to the second electrode. In some examples, the first and second reactive groups are selected from the group consisting of: amines, isothiocyanides, phosphines, carboxyls, selenos, pyridines, and methylsulfides. Additionally, or alternatively, the method in some examples further includes applying a bias voltage across the electrically conductive bridges that disrupts the transient bond between the first reactive group and the first electrode or the transient bond between the second reactive group and the second electrode. In some examples, the bias voltage disrupts the transient bond between the first reactive group and the first electrode and the transient bond between the second reactive group and the second electrode.

In some examples, the method further includes acting, using a polymerase coupled adjacent to the first and second electrodes, on a nucleotide coupled to one of the electrically conductive labels. That electrically conductive label forms one of the electrically conductive bridges responsive to the action, using the polymerase, on the nucleotide. In some examples, a particle is coupled to the first and second electrodes and to the polymerase. In some examples, the particle is electrically nonconductive.

Provided in some examples herein is a composition that includes first and second electrodes separated from one another by a space. A bridge spans the space between the first and second electrodes. The composition includes a fluid including a label that transiently bonds to the bridge in such a manner as to form an electrically conductive bridge. The composition includes detection circuitry to generate a signal responsive to formation of the electrically conductive bridge, and to generate a bias voltage selected to disrupt the electrically conductive bridge following generation of the signal.

Provided in some examples herein is a method for detecting. The method includes forming an electrically conductive bridge using transiently bonding of a label to a bridge spanning a space between first and second electrodes. The method includes detecting formation of the electrically conductive bridge. The method includes subsequently disrupting the transient bonding responsive to application of a bias voltage.

Provided in some examples herein is a composition that includes first and second electrodes separated from one another by a space. The composition includes first and second bridges spanning the space between the first and second electrodes. The first bridge includes a first polymer chain, and the second bridge includes a second polymer chain that is different from the first polymer chain. The composition includes a fluid including a first oligomer that is hybridizes to the first polymer chain and not to the second polymer chain. The composition includes detection circuitry configured to generate a first signal responsive to hybridization of the first oligomer to the first polymer chain.

In some examples, the fluid further includes a second oligomer that hybridizes to the second polymer chain and not to the first polymer chain. The detection circuitry is to generate a second signal responsive to hybridization of the second oligomer to the second polymer chain. In some examples, the detection circuitry further is to distinguish between hybridization of the first oligomer with the first polymer chain and hybridization of the second oligomer with the second polymer chain using at least a difference between the first signal and the second signal.

In some examples, the first and second polymer chains include different portions of a tertiary structure. In some examples, the tertiary structure includes a polynucleotide or polypeptide tertiary structure. The first and second polymer chains respectively may include first and second single stranded DNA sequences. The first and second oligomers respectively may include third and fourth single stranded DNA sequences that respectively complement the first and second single stranded DNA sequences.

In some examples, the tertiary structure includes a polypeptide.

Provided in some examples herein is a method for sequencing. The method includes adding, using a polymerase, nucleotides to a first polynucleotide using at least a sequence of a second polynucleotide. The method includes hybridizing a first label coupled to a first one of the nucleotides to a first polymer chain of a bridge spanning a space between first and second electrodes responsive to the polymerase adding that nucleotide to the first polynucleotide. The method includes sequentially hybridizing a second label coupled to a second one of the nucleotides to a second polymer chain of a bridge spanning a space between first and second electrodes. The method includes detecting the sequence in which the polymerase adds the first one of the nucleotides and the second one of the nucleotides to the first polynucleotide using at least changes in current through the bridge that are responsive to respective hybridizations between the first label with the first polymer chain and the second label with the second polymer chain.

In some examples, the first label does not hybridize with the second polymer chain, and the second label does not hybridize with the first polymer chain.

In some examples, the first and second labels include respective polymers.

In some examples, the first and second polymer chains include different portions of a tertiary structure.

In some examples, the tertiary structure includes a polynucleotide or polypeptide tertiary structure. The first and second polymer chains respectively may include first and second single stranded DNA sequences. The first and second labels respectively may include third and fourth single stranded DNA sequences that respectively complement the first and second single stranded DNA sequences.

In some examples, the tertiary structure includes a polypeptide.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

BRIEF DESCRIPTION OF DRAWINGS

FIG. 4 illustrates an example flow of operations in a method for making the devices of FIG. 1A-1B, 2, or 3A-3D.

FIG. 5 schematically illustrates an example operation in the method of FIG. 4.

FIG. 10 illustrates an example flow of operations in a method for sequencing a polynucleotide using any of the compositions of FIG. 8A-8B or 9A-9B.

FIG. 11C illustrates an example flow of additional operations in a method for preparing a device such as illustrated in FIG. 3B.

DETAILED DESCRIPTION

Figures 1A, 1B:
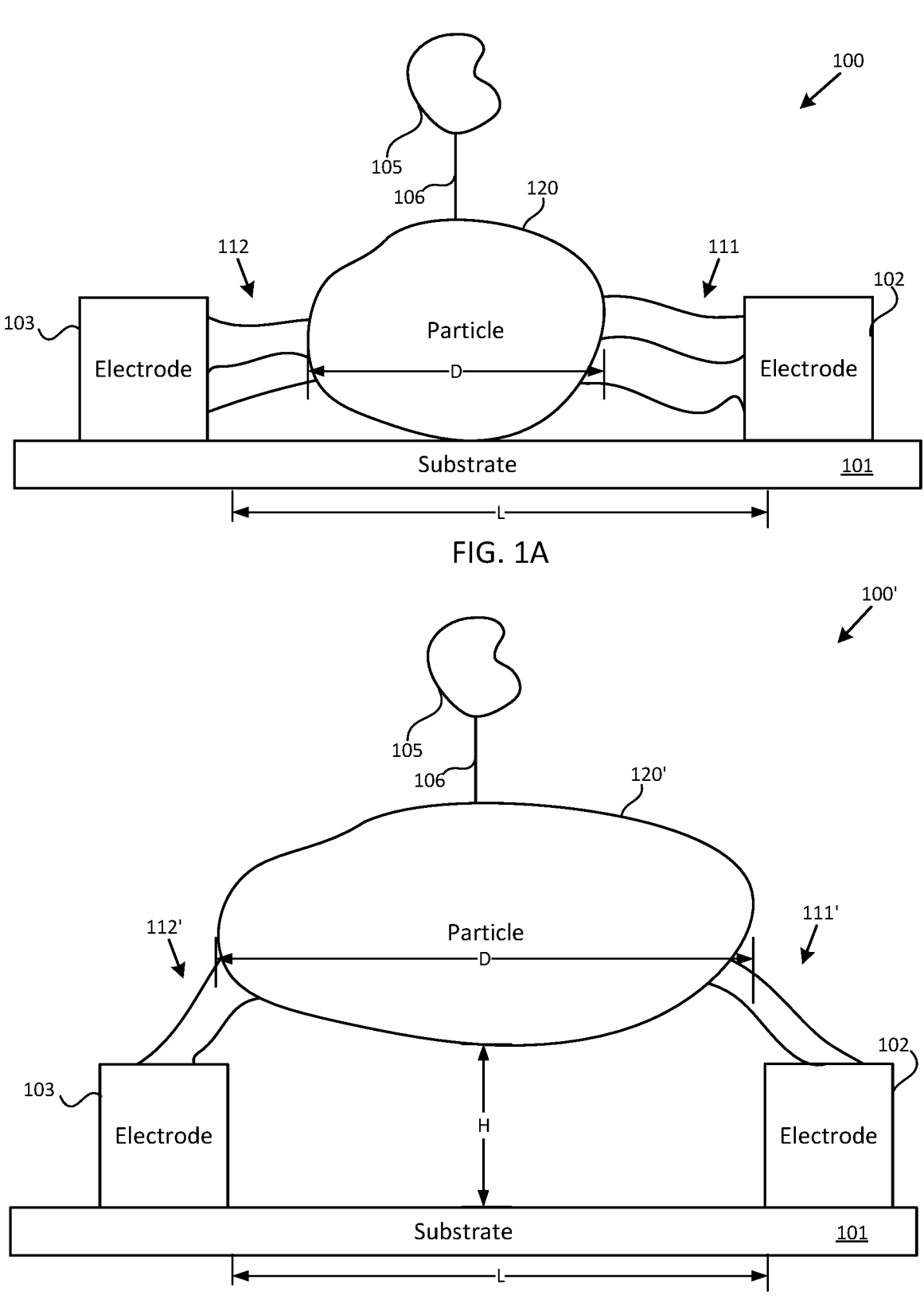
FIGS. 1A-1B schematically illustrate example devices including a particle-based bridge between electrodes.

Examples provided herein are related to electronically sequencing polynucleotides using particle-based bridges between electrodes. Compositions and methods for performing electronic sequencing are disclosed, as are devices including particle-based bridges and methods of forming such devices, and arrays of such devices.

More specifically, the present compositions, devices, and methods suitably may be used to sequence polynucleotides in a manner that is robust, reproducible, sensitive, and has high throughput. For example, the present devices can include a particle that is coupled to first and second electrodes. The particle may facilitate measuring changes in a current between those electrodes. In some examples, a polynucleotide may be sequenced using at least those changes. More specifically, the polynucleotide may be sequenced using detection of transient changes in electrical conductivity that arise from interactions of a nucleotide with the electrode bridge during a nucleotide incorporation event. One or more of those nucleotides (and in some examples all of those nucleotides) respectively are coupled to labels that cause distinct change in current between the electrodes, based upon which change the respective nucleotide may be identified. Nucleotides modified with labels may alter electrical conductivity of the bridge via a number of intermolecular interactions, including but not limited to hydrogen bonding, pi-pi stacking, and electrostatic interactions. In some examples, the labels respectively may hybridize to a polynucleotide bridge between the electrodes, and such hybridizations respectively may change the current through the bridge at levels that are unique to each particular nucleotide. In other examples, the label may interact with the bridge via a DNA intercalation mechanism. In other examples, the label may interact with the bridge via a DNA groove binding mechanism. The particle may, but need not necessarily, form part of such a bridge. In some examples, the labels may form transient bridges between the electrodes, and such bridges may provide different currents than one another based upon which the nucleotides respectively may be identified. In these and other examples, a polymerase may be coupled to the particle and may add the nucleotides to the growing complementary polynucleotide.

The present particle-based devices, compositions, and methods may be robustly fabricated and used. For example, electronic devices that include organic molecules (such as DNA, π-conjugated polymers, and the like), instead of particles, may be difficult to manufacture because of the probabilistic nature of assembling molecular components, e.g., performing bottom-up self-assembly of the organic molecules bridging two electrodes. The present disclosure, among other things, provides a method for assembling particle-based electronic devices in solution using wet chemistry techniques that localize the particles between respective electrodes. Such an approach allows for controllably placing the particles, and any functional groups coupled to the particles, within respective electronic devices. For example, the particles may include or be coupled to functional groups that possess an electrical functionality (e.g., polynucleotides such as DNA, π-conjugated polymers, or the like) or a biochemical functionality (e.g., enzyme, antigen, or the like), in some examples prior to coupling the particles to the electrodes. The devices may be used as sensors, e.g., biosensors that in some examples may be used for real-time sequencing of polynucleotides, with single-molecule sensitivity. For example, the functional groups may facilitate single-molecule analyte detection via changes in electrical conductivity between the electrodes of the device.

As described in greater detail below, some examples provide that the particles may be localized within respective devices using "passive" adsorption in which single particles are captured within or adjacent the space between electrodes, for example using at least surface interactions between the particles and electrodes. Some examples provide that the particles may be localized within respective devices using "active" adsorption, which may be referred to herein as dielectrophoretic trapping, in which a direct current (DC) or alternating current (AC) electrical bias is applied across the electrodes to accelerate trapping of single particles within or adjacent to the space between those electrodes. In other examples, the particles may include a magnetic or ferromagnetic material and may be localized within respective device by applying a magnetic field.

In some examples, the particles respectively may be covalently bonded to one or more surfaces of electrodes, in some examples via a plurality of bonds between the particle and each of the electrodes of the device. The bonds between the particles and the electrodes may be direct, or may be indirect via intermediate structure(s), e.g., functional groups, such as described elsewhere herein. For example, metal (e.g., gold) nanoparticles may include functional groups such as electrically conductive polynucleotide (e.g., DNA) duplexes with peripheral reactive groups, such as disulfide or thiol groups, which may covalently bond to electrodes (e.g., gold electrodes) to provide an electrically conductive bridge between the electrodes.

Some terms used herein will be briefly explained. Then, some example compositions and example methods for electronically sequencing polynucleotides will be described.

Terms

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The terms "substantially", "approximately", and "about" used throughout this Specification are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

As used herein the term "particle" is intended to mean a structure that is made up of a large number of atoms (e.g., more than about 100 atoms) and has a three dimensional structure with at least one external dimension being larger than about 5 nm. In some examples, a particle has a three dimensional structure with at least two external dimensions being larger than about 5 nm. In some examples, a particle has a three dimensional structure with all three external dimensions being larger than about 5 nm.

In some examples, a particle may act as a single unit with regards to its translational transport properties in a fluid. For example, translational movement of a first portion of the particle causes other portions of the particle to translationally move concurrently in the fluid. In comparison, an elongated, flexible, two-dimensional structure (such as a polymer lacking tertiary structure) may not necessarily act as a single unit with regards to its translational transport properties a fluid. For example, translational movement of a first end of such a structure may not cause translational movement of a second end of such a structure.

Some particles herein may include, or may consist of, a single molecule such as a polymer that has a tertiary structure. As used herein, a particle with "tertiary structure" is intended to mean a particle that is folded into a three-dimensional tertiary structure having internal cross-linking holding the folds in place. In comparison, a polymer that has a primary structure (e.g., a particular sequence of monomers linked together) and a secondary structure (e.g., local structure) but no internal cross-linking holding folds into place would not be considered to have a tertiary structure as the term is used herein, nor would that polymer be considered to be a particle as the term is used herein. For example, a double-stranded polynucleotide (e.g., dsDNA), a single-stranded polynucleotide (e.g., ssDNA), or a partially double-stranded (e.g., part dsDNA and part ssDNA) that has a primary structure (a particular sequence of bases in each of the strands) and a secondary structure (e.g., a double helix) but that is not folded and cross-linked into a tertiary structure is not considered to be a "particle" as the term is used herein. In comparison, a single-stranded, double-stranded, or partially double-stranded polynucleotide with a tertiary structure, or a polypeptide chain with a tertiary structure, may be considered to be a "particle" as the term is used herein.

Particles herein may include, or may consist of, a collection of discrete atoms or molecules that are attached to one another, e.g., are bonded to one another. An example of such a particle is a nanoparticle. Nanoparticles have one or more outer dimensions in the range of about 5 to about 100 nm, or two or more outer dimensions in the range of about 5 to about 100 nm, and in some examples have all outer dimensions in the range of about 5 to about 100 nm. By "outer dimension" it is meant a distance between outer surfaces of a particle in one direction. Nanoparticles may be spherical, or may be aspherical. Spherical or approximately spherical nanoparticles may have a diameter of about 5 to about 100 nm. Aspherical nanoparticles may be regularly shaped, e.g., may be elongated, or may be irregularly shaped. Aspherical nanoparticles may be referred to as having a diameter, even though they are not spherical. The diameter of an aspherical particle may refer to an average value of at least one dimension of the particle, and in some examples may refer to an average value of all dimensions of the particle. An elongated nanoparticle may have a diameter of about 5 to about 100 nm and a length greater than about 100 nm.

Particles may be electrically conductive, semiconductive, or electrically nonconductive (e.g., may be electrical insulators). Particles may include any suitable material or combination of materials. Electrically conductive particles may include, for example, gold, platinum, carbon, silver, palladium, or the like. Semiconductive particles may include one or more materials including, for example, cadmium, zinc, titanium, mercury, manganese, sulfur, selenium, tellurium, carbon, or the like. Electrically nonconductive particles may include, for example, silicon oxide, iron oxide, aluminum oxide, organic polymers, proteins, or the like.

Particles may include or may be coupled to functional groups. By "functional group" it is meant a molecular moiety that has one end bonded to the surface of the particle and has another end extending away from the surface of the molecule which may bond to another structure.

As used herein, the term "electrode" is intended to mean a solid structure that conducts electricity. Electrodes may include any suitable electrically conductive material, such as gold, platinum, or palladium.

As used herein, the term "bridge" is intended to mean a structure that extends between, and attaches to, other structures. A bridge may span a space between other structures. A bridge may be at least partially unsupported within that space, except for locations at which the bridge attaches to the other structures. A bridge may include multiple components which are attached to one another in such a manner as to extend between, and collectively connect to, other structures. A bridge may be attached to another structure, such as an electrode, via a chemical bond, e.g., via a covalent bond, hydrogen bond, ionic bond, dipole-dipole bond, London dispersion forces, or any suitable combination thereof.

As used herein, "transient" is intended to mean temporary, or not permanent.

As used herein, an element being "adjacent" to another element is intended to mean sufficiently close as to directly or indirectly interact with that other element.

As used herein, a "polymer" refers to a molecule including a chain of many subunits that are coupled to one another and that may be referred to as monomers. The subunits may repeat, or may differ from one another. Polymers can be biological or synthetic polymers. Example biological polymers that suitably can be included within a bridge or a label include polynucleotides, polypeptides, polysaccharides, polynucleotide analogs, and polypeptide analogs. Example polynucleotides and polynucleotide analogs suitable for use in a bridge or a label include DNA, enantiomeric DNA, RNA, PNA (peptide-nucleic acid), morpholinos, and LNA (locked nucleic acid). Polymers may include spacer phosphoramidites, which may be coupled to polynucleotides but which lack nucleobases, such as commercially available from Glen Research (Sterling, VA). Example synthetic polypeptides can include charged or neutral amino acids as well as hydrophilic and hydrophobic residues. Example synthetic polymers that suitably can be included within a bridge or label include PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly(ω-alkenoic acid esters), poly(alkyl methacrylates), and other polymeric chemical and biological linkers. Synthetic polymers may be electrically conductive, semiconductive, or insulating.

As used herein, "hybridize" is intended to mean noncovalently attaching a first polynucleotide to a second polynucleotide along the lengths of those polynucleotides via specific hydrogen bonding pairing of nucleotide bases. The strength of the attachment between the first and second polynucleotides increases with the length and complementarity between the sequences of monomer units within those polymers. For example, the strength of the attachment between a first polynucleotide and a second polynucleotide increases with the complementarity between the sequences of nucleotides within those polynucleotides, and with the length of that complementarity.

As used herein, the term "nucleotide" is intended to mean a molecule that includes a sugar and at least one phosphate group, and in some examples also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

As used herein, the term "nucleotide" also is intended to encompass any nucleotide analogue which is a type of nucleotide that includes a modified nucleobase, sugar and/or phosphate moiety compared to naturally occurring nucleotides. Example modified nucleobases include inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

As used herein, the term "polynucleotide" refers to a molecule that includes a sequence of nucleotides that are bonded to one another. A polynucleotide is one nonlimiting example of a polymer. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA or double stranded RNA, or can include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. Polynucleotides can include non-naturally occurring DNA, such as enantiomeric DNA. The precise sequence of nucleotides in a polynucleotide can be known or unknown. The following are example examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, a "polymerase" is intended to mean an enzyme having an active site that assembles polynucleotides by polymerizing nucleotides into polynucleotides. A polymerase can bind a primed single stranded polynucleotide template, and can sequentially add nucleotides to the growing primer to form a polynucleotide having a sequence that is complementary to that of the template.

As used herein, the term "primer" is defined as a polynucleotide having a single strand with a free 3' OH group. A primer can also have a modification at the 5' terminus to allow a coupling reaction or to couple the primer to another moiety. The primer length can be any number of bases long and can include a variety of non-natural nucleotides. A primer can be blocked at the 3' end to inhibit polymerization until the block is removed.

As used herein, the term "label" is intended to mean a structure that causes an electrical conductivity change between two electrodes. A label may attach to a bridge between two electrodes in such a manner as to cause an electrical conductivity change of that bridge, based upon which electrical conductivity change the nucleotide may be identified. For example, a label may hybridize to a polymer chain within such a bridge, and the hybridization may cause the electrical conductivity change. Or, a label may attach to each of two electrodes in such a manner as to cause an electrical conductivity change between those electrodes. In examples provided herein, labels can be attached to nucleotides.

As used herein, the term "substrate" refers to a material used as a support for compositions described herein. Example substrate materials may include glass, silica, plastic, quartz, metal, metal oxide, organo-silicate (e.g., polyhedral organic silsesquioxanes (POSS)), polyacrylates, tantalum oxide, complementary metal oxide semiconductor (CMOS), or combinations thereof. An example of POSS can be that described in Kehagias et al., Microelectronic Engineering 86 (2009), pp. 776-778, which is incorporated by reference in its entirety. In some examples, substrates used in the present application include silica-based substrates, such as glass, fused silica, or other silica-containing material. In some examples, silica-based substrates can include silicon, silicon dioxide, silicon nitride, or silicone hydride. In some examples, substrates used in the present application include plastic materials or components such as polyethylene, polystyrene, poly(vinyl chloride), polypropylene, nylons, polyesters, polycarbonates, and poly(methyl methacrylate). Example plastics materials include poly(methyl methacrylate), polystyrene, and cyclic olefin polymer substrates. In some examples, the substrate is or includes a silica-based material or plastic material or a combination thereof. In particular examples, the substrate has at least one surface including glass or a silicon-based polymer. In some examples, the substrates can include a metal. In some such examples, the metal is gold. In some examples, the substrate has at least one surface including a metal oxide. In one example, the surface includes a tantalum oxide or tin oxide. Acrylamides, enones, or acrylates may also be utilized as a substrate material or component. Other substrate materials can include, but are not limited to gallium arsenide, indium phosphide, aluminum, ceramics, polyimide, quartz, resins, polymers and copolymers. In some examples, the substrate and/or the substrate surface can be, or include, quartz. In some other examples, the substrate and/or the substrate surface can be, or include, semiconductor, such as GaAs or ITO. The foregoing lists are intended to be illustrative of, but not limiting to the present application. Substrates can include a single material or a plurality of different materials. Substrates can be composites or laminates. In some examples, the substrate includes an organo-silicate material.

Substrates can be flat, round, spherical, rod-shaped, or any other suitable shape. Substrates may be rigid or flexible. In some examples, a substrate is a bead or a flow cell.

Substrates can be non-patterned, textured, or patterned on one or more surfaces of the substrate. In some examples, the substrate is patterned. Such patterns may include posts, pads, wells, ridges, channels, or other three-dimensional concave or convex structures. Patterns may be regular or irregular across the surface of the substrate. Patterns can be formed, for example, by nanoimprint lithography or by use of metal pads that form features on non-metallic surfaces, for example.

In some examples, a substrate described herein forms at least part of a flow cell or is located in or coupled to a flow cell. Flow cells may include a flow chamber that is divided into a plurality of lanes or a plurality of sectors. Example flow cells and substrates for manufacture of flow cells that can be used in methods and compositions set forth herein include, but are not limited to, those commercially available from Illumina, Inc. (San Diego, CA).

Example Compositions and Methods for
Sequencing Polynucleotides

FIGS. 1A-1B schematically illustrate example devices including a particle-based bridge between electrodes. In the example shown in FIG. 1A, device 100 includes first electrode 102, second electrode 103, particle 120, and polymerase 105. Polymerase 105 may be coupled to particle 120. For example, in one example polymerase 105 may be coupled to particle 120 via linker 106 in a manner such as known in the art. Attachment of polymerase 105 to particle 120 may be achieved, for example, via a number of chemical reactions including but not limited to alkyne/azide click, amine/aldehyde Schiff base, amine/epoxy, spy tag/spy catcher, biotin/streptavidin, thiol/alkene, copper-free click chemistry reactions (i.e. cyclooctyne/azide), Ni/NTA. In another example, the attachment of polymerase 105 to particle 120 may be achieved via non-covalent interactions including electrostatic binding or hydrogen bonding.

In this example, substrate 101 may support first electrode 102 and second electrode 103. First electrode 102 and second electrode 103 may be separated from one another by a space, e.g., a space of length L as indicated in FIG. 1A. The value of L may be, in some examples, from about 5 nm to about 1 μm, e.g., from about 5 nm to about 100 nm, e.g., from about 5 nm to about 50 nm, e.g., from about 20 nm to about 50 nm. First electrode 102 and second electrode 103 may have any suitable shape, and are not limited to the approximately rectangular shape suggested in FIG. 1A. For example, the sidewalls of first electrode 102 and second electrode 103 illustrated in FIG. 1A may be, but need not necessarily be, vertical or parallel to one another, and need not necessarily meet the top surfaces of such electrodes at a right angle. For example, first electrode 102 and second electrode 103 may be irregularly shaped, may be curved, or include any suitable number of obtuse or acute angles. In another example, the electrodes 102 and 103 may be co-planar with the substrate 101. In another example, the electrodes may be vertically stacked on top of each other and the space between them may be defined by a suitable insulating layer of thickness L. The value L may refer to the spacing (length) between the closest points of first electrode 102 and second electrode 103 to one another. The respective widths of first electrode 102 and second electrode 103 (e.g., in the dimension into and out of the plane illustrated in FIG. 1A) may be different than the length L. As such, the width of the space between electrodes 102, 103 may be different than L. For example, the respective widths of first electrode 102 and second electrode 103, at the closest points of first electrode 102 and second electrode 103 to one another, may be less than L, and as a result the width of the space between the electrodes may be smaller than the length of the space between the electrodes. For example, the width may be, from about 1 nm to about 1 μm, e.g., from about 1 nm to about 100 nm, e.g., from about 2 nm to about 50 nm, e.g., from about 4 nm to about 50 nm.

In the example illustrated in FIG. 1A, particle 120 is at least partially disposed, and in some examples is fully disposed, within the space between first electrode 102 and second electrode 103. In one example, particle 120 contacts substrate 101 in the space between first electrode 102 and second electrode 103. Particle 120 may have any suitable diameter. For example, in configurations in which particle 120 is at least partially disposed within the space between first electrode 102 and second electrode 103, particle 120 may have a diameter D that is less than L. For example, particle 120 may have a diameter D that is at least about 10% of L, a diameter D that is at least about 20% of L, a diameter D that is at least about 30% of L, a diameter D that is at least about 40% of L, a diameter D that is at least about 50% of L, a diameter D that is at least about 60% of L, a diameter D that is at least about 70% of L, a diameter D that is at least about 80% of L, a diameter D that is at least about 90% of L, a diameter D that is at least about 95% of L, or a diameter D that is less than about 100% of L. Diameter D may, for example, be in the range of about 10% to about 90% of L, or in the range of about 20% to about 90% of L, or in the range of about 50% to about 90% of L, or in the range of about 60% to about 80% of L. In some examples, particle 120 may have a diameter D that is less than the width of the space between first electrode 102 and second electrode 103. For example, particle 120 may have a diameter D that is at least about 10% of the width, a diameter D that is at least about 20% of the width, a diameter D that is at least about 30% of the width, a diameter D that is at least about 40% of the width, a diameter D that is at least about 50% of the width, a diameter D that is at least about 60% of the width, a diameter D that is at least about 70% of the width, a diameter D that is at least about 80% of the width, a diameter D that is at least about 90% of the width, a diameter D that is at least about 95% of the width, or a diameter D that is less than about 100% of the width. Diameter D may, for example, be in the range of about 10% to about 90% of the width, or in the range of about 20% to about 90% of the width, or in the range of about 50% to about 90% of the width, or in the range of about 60% to about 80% of the width.

Particle 120 may have any suitable composition. For example, particle 120 may be electrically conductive, e.g., may form at least part of an electrically conductive bridge between first electrode 102 and second electrode 103, for example in a manner such as described with reference to FIG. 2 or 3B-3D. Or, for example, particle 102 may be semiconductive or electrically nonconductive, e.g., in a manner such as described with reference to FIG. 3A. Examples of electrically conductive and electrically nonconductive materials suitable for use in the present particles are provided elsewhere herein.

Particle 120 may have any suitable shape. For example, in FIG. 1A particle 120 is suggested to be aspherical, particle 120 instead may be spherical or approximately spherical. Examples of shapes suitable for use with the present particles are provided elsewhere herein.

Particle 120 may be coupled to first electrode 102 via plurality of bonds 111 which in some examples include first functional groups extending between a first portion of particle 120 and first electrode 102, and coupled to second electrode 103 via plurality of bonds 112 which in some examples include second functional groups extending between a second portion of particle 120 and second electrode 103. Although the example shown in FIG. 1A suggests that all of bonds 111 and bonds 112 respectively are attached to vertical surfaces of electrodes 102 and 103 (in some examples via the first functional groups and second functional groups), it should be appreciated that any suitable number of such bonds instead may be attached to the respective top surfaces of the electrodes (in some examples via the first functional groups and second functional groups). Particle 120, bonds 111, bonds 112, and any functional groups coupled to the particle may span the space between first electrode 102 and second electrode 103. Bonds 111 may include any suitable bond or combination of bonds. Bonds 112 may include any suitable bond or combination of bonds. For example, bonds 111 and bonds 112 each, and independently from one another, may include a bond selected from the group consisting of covalent bond, hydrogen bond, ionic bond, dipole-dipole bond, London dispersion forces, and any suitable combination thereof. Bonds 111 and bonds 112 may be or include direct bonds between particle 120 and the respective electrode such as exemplified with reference to FIGS. 2, 3A, and 3D, or may include indirect bonds via one or more intermediate structures such as functional groups, e.g., as exemplified with reference to FIGS. 3B-3C.

In examples in which the present particle (e.g., particle 120 or other particle described herein) directly or indirectly is coupled to a first electrode via a plurality of bonds, and directly or indirectly is coupled to a second electrode via a plurality of bonds, the device may be electronically robust. For example, if current were to pass from an electrode into the particle via a single bond, and from the particle and into another electrode via a single bond, such current may cause either or both of those bonds to become hot and may break, thus damaging the device. In comparison, passing current from the electrode to the particle via a plurality of bonds, and from the particle to another electrode via a plurality of bonds, which pluralities of bonds may be distributed over the surface of the particle in a manner such as indicated in FIG. 1A, may distribute the current amongst those bonds, thus inhibiting overheating of the bonds and inhibiting damage to the device that otherwise may result from such overheating.

In the example shown in FIG. 1B, device 100' includes first electrode 102, second electrode 103, particle 120', and polymerase 105. Polymerase may be coupled to particle 120', in some examples via linker 106. In this example, substrate 101 may support first electrode 102 and second electrode 103, which may be separated from one another by a space in a manner such as described with reference to FIG. 1A. In the example illustrated in FIG. 1B, particle 120' is at least partially disposed, and in some examples is fully disposed, within the space above first electrode 102 and second electrode 103. For example, particle 120' may be disposed at a height H above substrate 101. The value of H may be, in some examples, from about 1 nm to about 100 nm, e.g., from about 1 nm to about 50 nm, e.g., from about 10 nm to about 50 nm. The value of H in some examples may be greater than the heights of one or both of electrodes 102, 103 (which heights may be, but need not necessarily be, approximately the same as one another), such that no portion of particle 120 is located vertically between the electrodes.

Particle 120' illustrated in FIG. 1B may have a composition and shape similar to that described for particle 120 described with reference to FIG. 1A, but may be sized similarly or differently as particle 120. For example, in configurations in which particle 120' is at least partially disposed within the space above first electrode 102 and second electrode 103, particle 120 may have a diameter D that is less than L, or may have a diameter D that is greater than L. For example, particle 120' may have a diameter D that is at least about 10% of L, a diameter D that is at least about 20% of L, a diameter D that is at least about 30% of L, a diameter D that is at least about 40% of L, a diameter D that is at least about 50% of L, a diameter D that is at least about 60% of L, a diameter D that is at least about 70% of L, a diameter D that is at least about 80% of L, a diameter D that is at least about 90% of L, a diameter D that is at least about 95% of L, or a diameter D that is at least about 100% of L, or a diameter D that is at least about 110% of L, or a diameter D that is at least about 120% of L, or a diameter D that is at least about 130% of L, or a diameter D that is at least about 150% of L, or a diameter D that is at least about 200% of L, or a diameter of at least about 300% of L, or a diameter of at least about 400% of L, or a diameter of at least about 500% of L. Diameter D may, for example, be in the range of about 10% to about 500% of L, or in the range of about 20% to about 400% of L, or in the range of about 50% to about 300% of L, or in the range of about 60% to about 200% of L, or in the range of about 70% to about 100% of L.

Particle 120' may be coupled to first electrode 102 via plurality of bonds 111' (in some examples including first functional groups), and coupled to second electrode 103 via plurality of bonds 112' (in some examples including second functional groups). In the example shown in FIG. 1B, one or more of bonds 111' and bonds 112', and in some examples all of bonds 111' and 112', respectively are attached to respective top (horizontal) surfaces of electrodes 102 and 103. Particle 120', bonds 111', and bonds 112' may span the space between first electrode 102 and second electrode 103. In some examples, particle 120' contacts one or both of first electrode 102 and second electrode 103 and is bonded directly thereto, while in other examples, particle 120' is indirectly bonded to first and second electrodes 102, 103 via intermediate structure(s) such as functional groups.

Figure 2:
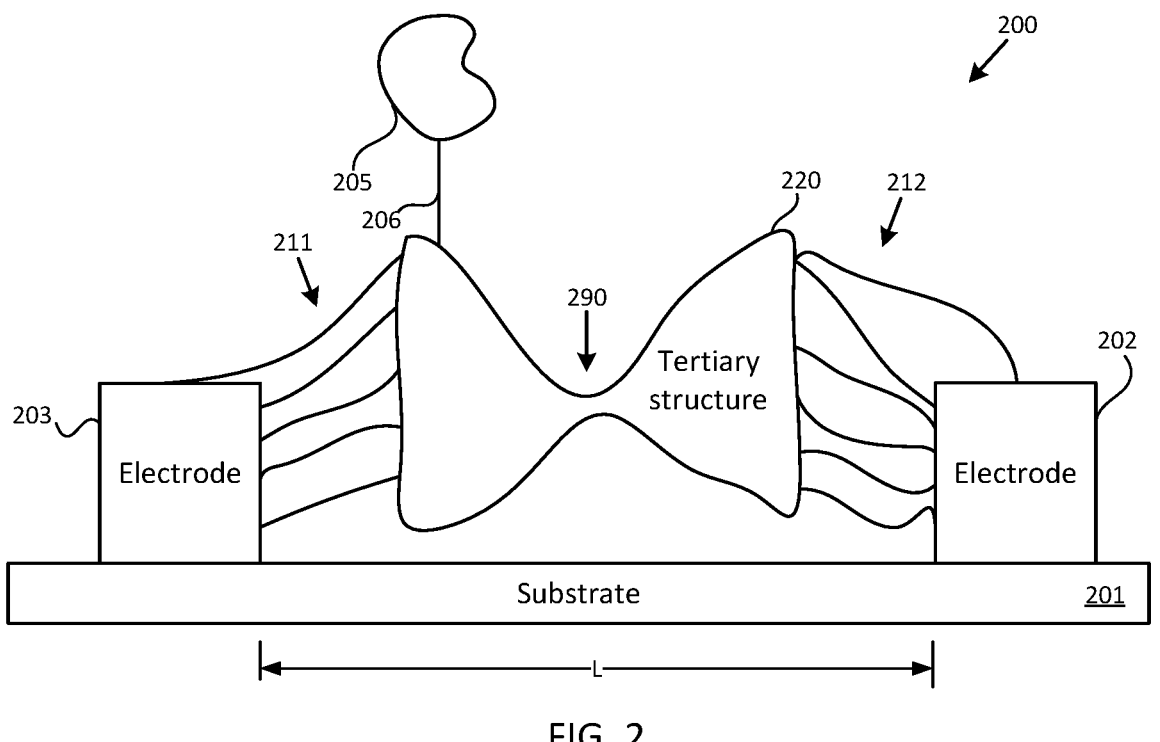
FIG. 2 schematically illustrates an example device including a tertiary polymer structure between electrodes.

In some examples, particle 120 illustrated in FIG. 1A or particle 120' illustrated in FIG. 1B includes a polymer having a tertiary structure. FIG. 2 schematically illustrates an example device 200 including a tertiary polymer structure between electrodes. In the example shown in FIG. 2, device 200 includes first electrode 202, second electrode 203, tertiary polymer structure 220, and polymerase 205. Polymerase 205 may be coupled to tertiary polymer structure 220. For example, polymerase 205 in some examples may be coupled to tertiary polymer structure 220 via linker 206 in a manner such as known in the art. For example, polymerase 205 may be attached to tertiary polymer structure 206 via a number of chemical reactions including but not limited to alkyne/azide click, amine/aldehyde Schiff base, amine/epoxy, spy tag/spy catcher, biotin/streptavidin, thiol/alkene, copper free click reactions (i.e. cyclooctyne/azide), Ni/NTA. Alternatively the attachment of polymerase 205 to tertiary polymer structure 206 may be achieved via non-covalent interactions including electrostatic binding or hydrogen bonding.

In this example, substrate 201 may support first electrode 202 and second electrode 203. First electrode 202 and second electrode 203 may be separated from one another by a space, e.g., a space of length L as indicated in FIG. 2, and may have any suitable shape such as described in greater detail with reference to FIG. 1A. The value of L may be, in some examples, from about 5 nm to about 1 μm, e.g., from about 10 nm to about 100 nm, e.g., from about 10 nm to about 50 nm, e.g., from about 20 nm to about 50 nm. In the example illustrated in FIG. 2, tertiary polymer structure 220 is at least partially disposed, and in some examples is fully disposed, within the space between first electrode 202 and second electrode 203 in a manner such as described with reference to FIG. 1A. In some examples, tertiary polymer structure 220 contacts substrate 201 in the space between first electrode 202 and second electrode 203. Tertiary polymer structure 220 may be at least partially disposed, and in some examples is fully disposed, above the space between first electrode 202 and second electrode 203 in a manner such as described with reference to FIG. 1B. That is, tertiary polymer structure 220 may have any suitable height above substrate 201, and may have any suitable diameter, such as those exemplified with reference to FIGS. 1A-1B.

Tertiary polymer structure 220 may have any suitable composition. In some examples, tertiary polymer structure includes a polynucleotide, such as DNA, or a polypeptide. In the nonlimiting example illustrated in FIG. 2, the polynucleotide or polypeptide may be folded and cross-linked into a tertiary structure having central constriction 290, e.g., a relatively narrow region between wider regions that respectively are attached to electrodes 202, 203 at multiple points. In some examples, central constriction 290 forms part of an electrically conductive bridge between the first and second electrodes. For example, tertiary polymer structure 220 may be electrically conductive, e.g., may form at least part of an electrically conductive bridge between first electrode 202 and second electrode 203. The electrical conductivity of the bridge through central constriction 290 in some examples may be modulated, e.g., in a manner such as described with reference to FIG. 9B. In one nonlimiting configuration, tertiary polymer structure 220 includes, or consists of, a single molecule.

Tertiary polymer structure 220 may be coupled to first electrode 202 via plurality of bonds 211, and coupled to second electrode 203 via plurality of bonds 212. Although the example shown in FIG. 2 suggests that a mixture of bonds 211 and bonds 212 respectively are attached to vertical or horizontal surfaces of electrodes 202 and 203, it should be appreciated that any suitable combination of such bonds instead may be attached to top or vertical surfaces of respective electrodes. Tertiary polymer structure 220, bonds 211, and bonds 212 may span the space between first electrode 202 and second electrode 203. Bonds 211 may include any suitable bond or combination of bonds. Bonds 212 may include any suitable bond or combination of bonds. For example, bonds 211 and bonds 212 each, independently from one another, may include a bond selected from the group consisting of covalent bond, hydrogen bond, ionic bond, dipole-dipole bond, London dispersion forces, and any suitable combination thereof. Bonds 211 and 212 may be or include direct bonds between tertiary polymer structure 220 and the respective electrode. For example, the tertiary polymer structure may include functional groups to bond the structure to the respective electrodes. By using a tertiary polymer structure (such as DNA origami) of a size and shape that is tailored to the specific length of the space between electrodes, such a space may be functionalized with exactly one such structure. Once the tertiary polymer structure is in place, it may inhibit any further tertiary polymer structure from entering the space due to steric or geometric exclusion.

In some configurations, the polymer of tertiary polymer structure 220 is or includes DNA. In some examples, "DNA origami," meaning DNA with an intended tertiary structure, may be constructed by mixing a single long DNA molecule, which may be referred to as a "template," with short complementary sequences which may be called "staples." Each staple may bind to specific regions within the long DNA molecule and pull the long DNA molecule into a desired shape, a nonlimiting example of which is illustrated in FIG. 2. Each staple may have a unique sequence and may end up in a well-defined location in the final tertiary structure. Because every staple may be individually functionalized independently from any functionalization of other staples, this allows for exact placement of specific functional elements on the tertiary structure, such as a functional element that may be used to couple a polymerase, or a functional element that may be used to bond to an electrode. Example functional elements that may be included in or attached to one or more staples include, but are not limited to, nanoparticles, enzymes, chemical linkers, molecular wires such as carbon nanotubes, peptides, or other DNA origamis or DNA sequences. Relatively large DNA origami structures may be formed from multiple, smaller DNA origami structures. For further details regarding DNA origami design and preparation, see the following reference, the entire contents of which are incorporated by reference herein: Wang et al., "The Beauty and Utility of DNA Origami," Chem 2: 359-382 (2017).

In one nonlimiting example, the high precision with which functional elements may be positioned on a DNA origami may offer a number of different applications that may facilitate polynucleotide sequencing. For example, metal nanoparticles of selected sizes and compositions may be disposed at well defined locations on the DNA origami. At distances of a few nanometers from one another, the metallic nanoparticles may exhibit nanoplasmonic effects, such as near-field coupling between nanoparticles. For further details on nanoplasmonic effects of metallic nanoparticles, see the following reference, the entire contents of which are incorporated by reference herein: Danckwerts et al., "Optical frequency mixing at coupled gold nanoparticles," Phys. Rev. Lett. 98: 026104 (2007). The present devices may be used with any suitable type of particle. For example, FIGS. 3A-3D schematically illustrate example devices including nanoparticle-based bridges between electrodes. In the example shown in FIG. 3A, device 300 includes first electrode 302, second electrode 303, nanoparticle 320, and polymerase 305. Polymerase 305 may be coupled to nanoparticle 320. For example, polymerase 305 may be coupled to nanoparticle 320 via a linker 306, or directly as suggested in FIG. 3A. In this example, substrate 301 may support first electrode 302 and second electrode 303. First electrode 302 and second electrode 303 may be separated from one another by a space, e.g., a space of length L, and may have any suitable shape, for example such as described in greater detail with reference to FIG. 1A. The value of L may be, in some examples, from about 5 nm to about 1 μm, e.g., from about 10 nm to about 100 nm, e.g., from about 10 nm to about 50 nm, e.g., from about 30 nm to about 50 nm. In the example illustrated in FIG. 3A, nanoparticle 320 is at least partially disposed, and in some examples is fully disposed, within the space between first electrode 302 and second electrode 303 in a manner such as described with reference to FIG. 1A. In the example illustrated in FIG. 3A, nanoparticle 320 contacts substrate 301 in the space between first electrode 302 and second electrode 303. However, it should be understood that nanoparticle 320 may be at least partially disposed, and in some examples is fully disposed, above the space between first electrode 302 and second electrode 303 in a manner such as described with reference to FIG. 1B. That is, nanoparticle 320 may have any suitable height above substrate 301, and may have any suitable diameter, such as those exemplified with reference to FIGS. 1A-1B. In the example specifically illustrated in FIG. 3A, nanoparticle 320 may have a diameter that is approximately equal to the length of the space between electrodes 302, 303.

Nanoparticle 320 may be coupled to first electrode 302 via plurality of bonds 311, and coupled to second electrode 303 via plurality of bonds 312. Although the example shown in FIG. 3A suggests that bonds 311 and bonds 312 are attached to vertical surfaces of electrodes 302 and 303, it should be appreciated that any suitable combination of such bonds instead may be attached to top or vertical surfaces of respective electrodes. Nanoparticle 320, bonds 311, and bonds 312 may span the space between first electrode 302 and second electrode 303. Bonds 311 may include any suitable bond or combination of bonds. Bonds 312 may include any suitable bond or combination of bonds. For example, bonds 311 and bonds 312 each, and independently from one another, may include a bond selected from the group consisting of covalent bond, hydrogen bond, ionic bond, dipole-dipole bond, London dispersion forces, and any suitable combination thereof. In the example shown in FIG. 3A, bonds 311 and 312 are or include direct bonds between nanoparticle 320 and the respective electrode. For example, nanoparticle 320 includes functional groups to bond the structure to the respective electrodes.

Nanoparticle 320 may have any suitable composition. In some examples, nanoparticle 320 is inorganic. Examples of materials suitable for use in nanoparticles, including inorganic materials, are provided elsewhere herein. Nanoparticle 320 in some examples may be electrically nonconductive, such that electrical current substantially does not pass through nanoparticle 320 between first electrode 302 and second electrode 303. Examples of electrically nonconductive materials suitable for use in the present particles are provided elsewhere herein. In some examples, in a manner such as described with reference to FIG. 9A, structures such as labels respectively may be used to form electrically conductive bridges between first electrode 302 and second electrode 303.

Figure 3A:
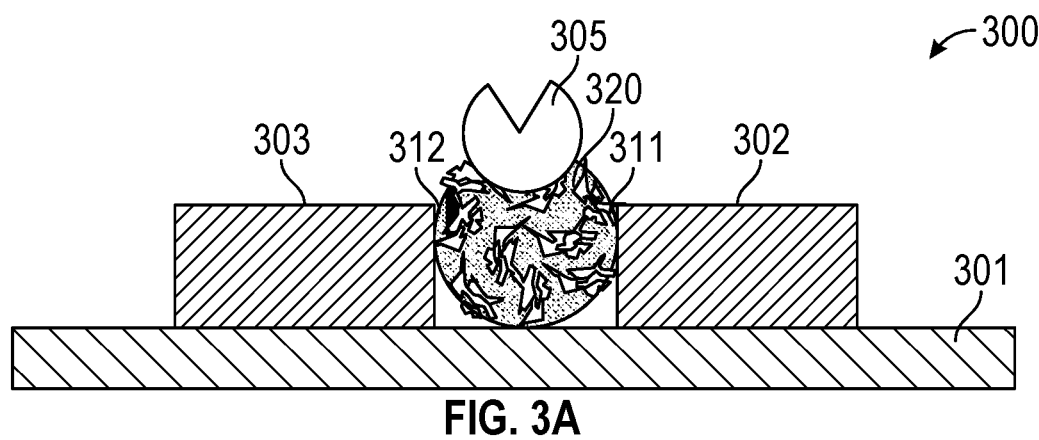
FIGS. 3A-3D schematically illustrate example devices including nanoparticle-based bridges between electrodes.
Figure 3B:
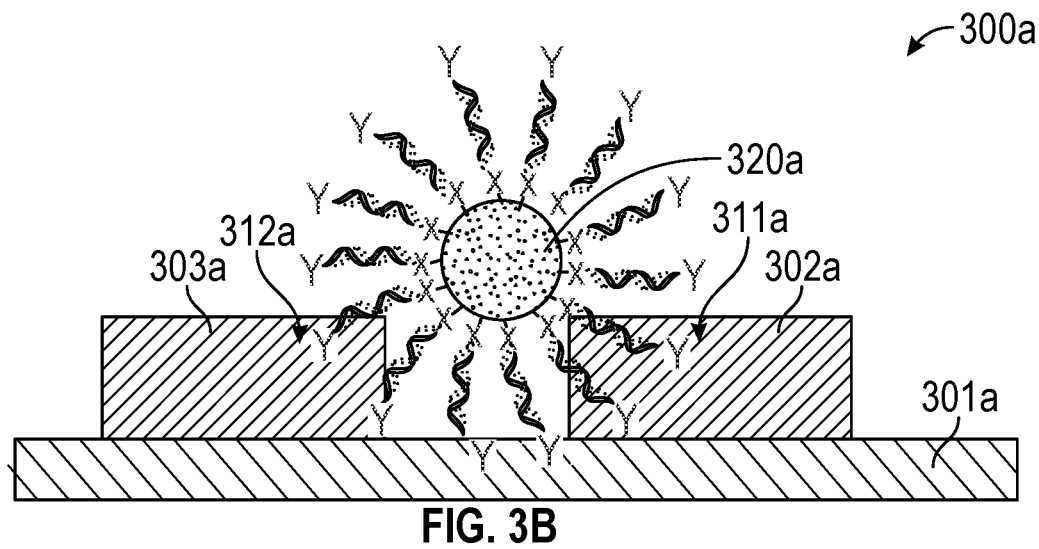

In the example shown in FIG. 3B, device 300a includes first electrode 302a, second electrode 303a, nanoparticle 320a, and a polymerase coupled to nanoparticle 320 in a manner similar to that described elsewhere herein (polymerase not specifically shown in FIG. 3B). In this example, substrate 301a may support first electrode 302a and second electrode 303a. First electrode 302a and second electrode 303a may be separated from one another by a space, e.g., a space of length L, and may have any suitable shape, for example such as described in greater detail with reference to FIG. 1A. In the example illustrated in FIG. 3B, nanoparticle 320a is at least partially disposed, and in some examples is fully disposed, above the space between first electrode 302a and second electrode 303a in a manner such as described with reference to FIG. 1B. That is, nanoparticle 320a may have any suitable height above substrate 301a, and may have any suitable diameter, such as those exemplified with reference to FIGS. 1A-1B.

Nanoparticle 320a may be coupled to first electrode 302a via plurality of functional groups 311a, and coupled to second electrode 303a via plurality of functional groups 312a. Any suitable combination of such functional groups may be attached to any suitable combination of top or vertical surfaces of respective electrodes. Nanoparticle 320a, functional groups 311a, and functional groups 312a may span the space between first electrode 302a and second electrode 303a. Functional groups 311a may include any suitable combination of bonds. Functional groups 312a may include any suitable combination of bonds. For example, functional groups 311a and functional groups 312a each, and independently from one another, may include a bond selected from the group consisting of covalent bond, hydrogen bond, ionic bond, dipole-dipole bond, London dispersion forces, and any suitable combination thereof. In the example shown in FIG. 3B, functional groups 311a and 312a provide indirect bonds between nanoparticle 320 and the respective electrode. For example, nanoparticle 320a includes functional groups including first oligonucleotides (such as DNA) that are attached to the material of nanoparticle via groups designated "X," and second oligonucleotides (such as DNA) that are hybridized to the first oligonucleotides. The second oligonucleotides may include reactive groups designated "Y," which may react with respective ones of first and second electrodes 302a, 303a so as to couple nanoparticle 320a to the electrodes, in some examples forming an electrically conductive bridge between the electrodes.

Nanoparticle 320a illustrated in FIG. 3B may have any suitable composition. In some examples, nanoparticle 320a is inorganic. Examples of materials suitable for use in nanoparticles, including inorganic materials, are provided elsewhere herein. Nanoparticle 320a in some examples may be electrically conductive, such that electrical current passes through nanoparticle 320a between first electrode 302a and second electrode 303a via the functional groups. Examples of electrically conductive materials suitable for use in the present particles are provided elsewhere herein. In some examples, the electrical conductivity between electrodes 302a, 303a may be modulated in a manner such as described with reference to FIGS. 8A-8B.

In one nonlimiting example, nanoparticle 320a (e.g., a gold nanoparticle) may be coupled to functional groups including DNA duplexes 311a, 312b bonding the nanoparticle to first electrode 302a and second electrode 303a. Here the DNA may play a role in the electrical conductivity between first electrode 302a and second electrode 303a, as DNA is known to exhibit electrical conductivity. Formation of the junction between nanoparticle 320a and electrodes 302a, 303a via functional groups such as DNA duplexes 311a, 312b may provide an electrically conductive path from one electrode to the other via the DNA duplexes. The reactive groups "Y" of DNA duplexes 311a, 312b may provide a corona capable of reacting with first electrode 302a and second electrode 303a, e.g., disulfide or thiol groups that react with the material (e.g., gold) of the electrodes to form sulfide bonds (e.g., Au—S), either directly through a gold-disulfide reaction or after being cleaved to thiol via a suitable reducing agent. Such a strategy may be applied to other nanoparticle compositions by choosing compatible groups to form the DNA-nanoparticle bond.

Figure 3C:
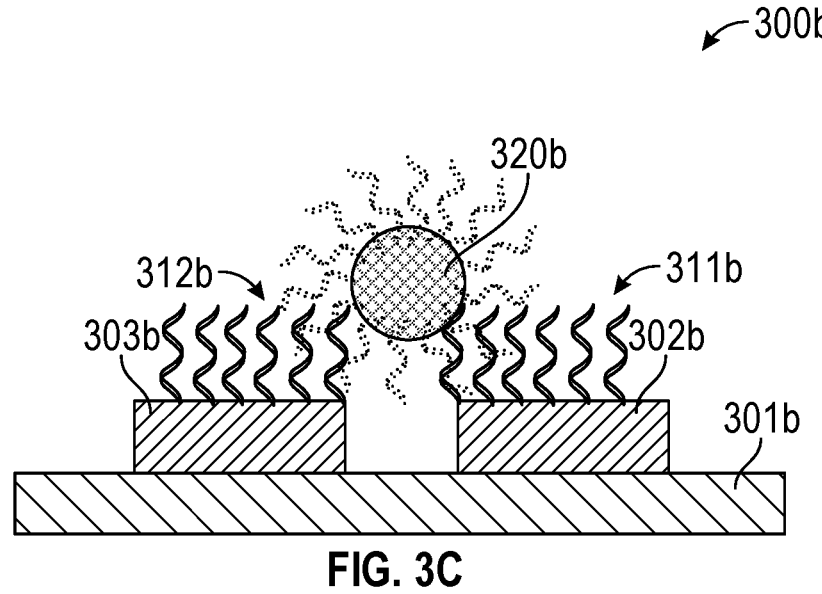

In the example shown in FIG. 3C, device 300b includes first electrode 302b, second electrode 303b, nanoparticle 320b, and a polymerase coupled to nanoparticle 320 in a manner similar to that described elsewhere herein (polymerase not specifically shown in FIG. 3B). In this example, substrate 301b may support first electrode 302b and second electrode 303b. First electrode 302b and second electrode 303b may be separated from one another by a space, e.g., a space of length L, and may have any suitable shape, for example such as described in greater detail with reference to FIG. 1A. In the example illustrated in FIG. 3C, nanoparticle 320b is at least partially disposed, and in some examples is fully disposed, above the space between first electrode 302b and second electrode 303b in a manner such as described with reference to FIG. 1B. That is, nanoparticle 320b may have any suitable height above substrate 301b, and may have any suitable diameter, such as those exemplified with reference to FIGS. 1A-1B.

Nanoparticle 320b may be coupled to first electrode 302b via a plurality of functional groups 311b, and coupled to second electrode 303b via plurality of functional groups 312b. Any suitable combination of such functional groups may be attached to any suitable combination of top or vertical surfaces of respective electrodes. Nanoparticle 320*b*, functional groups 311*b*, and functional groups 312*b* may span the space between first electrode 302*b* and second electrode 303*b*. Functional groups 311*b* may include any suitable combination of bonds. Functional groups 312*b* may include any suitable combination of bonds. For example, functional groups 311*b* and functional groups 312*b* each, and independently from one another, may include a bond selected from the group consisting of covalent bond, hydrogen bond, ionic bond, dipole-dipole bond, London dispersion forces, and any suitable combination thereof. In the example shown in FIG. 3C, functional groups 311*b* and 312*b* provide indirect bonds between nanoparticle 320 and the respective electrode. For example, nanoparticle 320*b* includes functional groups including first oligonucleotides (such as DNA) that are attached to the material of nanoparticle via respective groups (not specifically illustrated), and first and second electrodes 302*b*, 303*b* are attached to second oligonucleotides (such as DNA) that are hybridized to the first oligonucleotides so as to couple nanoparticle 320*b* to the electrodes, in some examples forming an electrically conductive bridge between the electrodes.

Nanoparticle 320*b* illustrated in FIG. 3C may have any suitable composition. In some examples, nanoparticle 320*b* is inorganic. Examples of materials suitable for use in nanoparticles, including inorganic materials, are provided elsewhere herein. Nanoparticle 320*b* in some examples may be electrically conductive, such that electrical current passes through nanoparticle 320*b* between first electrode 302*b* and second electrode 303*b* via the functional groups. Examples of electrically conductive materials suitable for use in the present particles are provided elsewhere herein. In some examples, the electrical conductivity between electrodes 302*b*, 303*b* may be modulated in a manner such as described with reference to FIGS. 8A-8B.

Figure 3D:
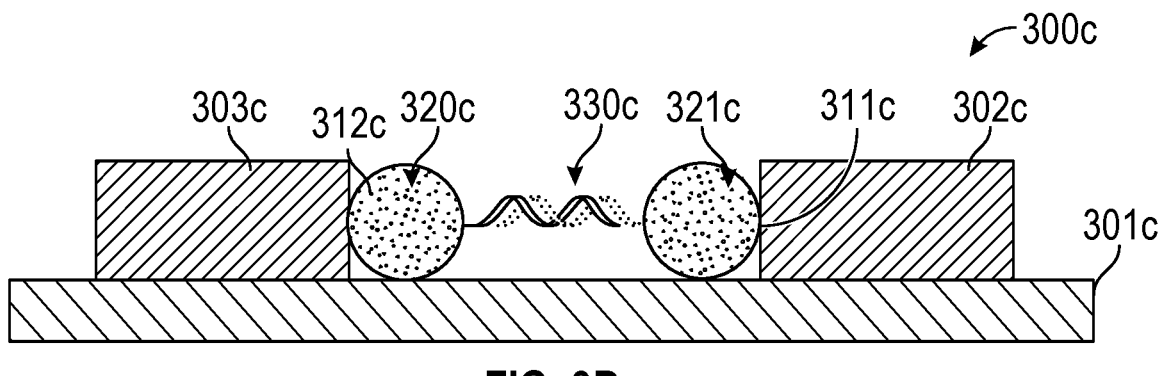

In the example shown in FIG. 3D, device 300*c* includes first electrode 302*c*, second electrode 303*c*, pair of nanoparticles 320*c*, 321*c* coupled together by linker 330*c*, and a polymerase coupled to nanoparticle 320 in a manner similar to that described elsewhere herein (polymerase not specifically shown in FIG. 3B). In this example, substrate 301*c* may support first electrode 302*c* and second electrode 303*c*. First electrode 302*c* and second electrode 303*c* may be separated from one another by a space, e.g., a space of length L, and may have any suitable shape, for example such as described in greater detail with reference to FIG. 1A. In the example illustrated in FIG. 3D, nanoparticle pair 320*c*, 321*c* is at least partially disposed, and in some examples is fully disposed, within the space between first electrode 302*c* and second electrode 303*c* in a manner such as described with reference to FIG. 1A. That is, nanoparticle pair 320*c*, 321*c* may have any suitable height above substrate 301*c*, and may have any suitable diameter, such as those exemplified with reference to FIGS. 1A-1B. In the example specifically illustrated in FIG. 3D, nanoparticle 320*c* may have a diameter that is less than 40% the length of the space between electrodes 302*c*, 303*c*, and nanoparticle 321*c* may have a diameter that is less than 40% the length of the space between electrodes 302*c*, 303*c*, such that nanoparticles 320*c* and 320*d* and linker 330*c* may fit within the space between the electrodes.

Nanoparticle 320*c* may be coupled to first electrode 302*c* via first plurality of bonds 311*c*, and nanoparticle 321*c* may be coupled to second electrode 303*c* via second plurality of bonds 312*c*. Any suitable combination of such bonds may be attached to any suitable combination of top or vertical surfaces of respective electrodes. Nanoparticle 320*c* may be linked to nanoparticle 321*c* via linker 330*c* which may include one or more functional groups. Nanoparticle 320*c*, nanoparticle 321*c*, bonds 311*c*, bonds 312*c*, and linker 330*c* may span the space between first electrode 302*c* and second electrode 303*c*. Bonds 311*c* may include any suitable bond or combination of bonds. Bonds 312*c* may include any suitable bond or combination of bonds. Linker 330*c* may include any suitable bond or combination of bonds. For example, bonds 311*c*, bonds 312*c*, and linker 330*c* each, and independently from one another, may include a bond selected from the group consisting of covalent bond, hydrogen bond, ionic bond, dipole-dipole bond, London dispersion forces, and any suitable combination thereof. In the example shown in FIG. 3D, bonds 311*c* are or include direct bonds between nanoparticle 320*c* and electrode 302*c*; bonds 312*c* are or include direct bonds between nanoparticle 321*c* and electrode 303*c*; and linker 330*c* includes indirect bonds between nanoparticle 320*c* and nanoparticle 321*c*. For example, in FIG. 3D, nanoparticle 320*c* is coupled to one or more functional groups including one or more first oligonucleotides (such as DNA) that are attached to the material of that nanoparticle via respective groups (not specifically illustrated), and nanoparticle 321*c* is coupled to one or more functional groups including one or more second oligonucleotides (such as DNA) that are attached to the material of that nanoparticle via respective groups (not specifically illustrated). The one or more second oligonucleotides are hybridized to the one or more first oligonucleotides so as to couple nanoparticle 320*b* to nanoparticle 321*c* via linker 330*c*, in some examples forming an electrically conductive bridge between the electrodes.

Nanoparticles 320*c*, 321*c* illustrated in FIG. 3D may have any suitable composition. In some examples, nanoparticles 320*c*, 321*c* are inorganic. Examples of materials suitable for use in nanoparticles, including inorganic materials, are provided elsewhere herein. Nanoparticles 320*c*, 321*c* in some examples may be electrically conductive, such that electrical current passes through nanoparticles 320*c* and 321*c* between first electrode 302*c* and second electrode 303*c*. Examples of electrically conductive materials suitable for use in the present particles are provided elsewhere herein. In some examples, the electrical conductivity between electrodes 302*c*, 303*c* may be modulated in a manner such as described with reference to FIGS. 8A-8B.

In one nonlimiting example, gold nanoparticles 320*c*, 321*c* and DNA linker 330*c* form a dumbbell shaped complex providing nanoparticle-molecular junction device 300*c*. The dumbbell shaped complex may be bound to a polymerase (not expressly illustrated) via a reactive group on DNA linker 330*c* (e.g., streptavidin to bind to a biotin coupled to the polymerase). The complex may be localized within the space between electrodes 302*c*, 303*c* using passive or active operations such as described in greater detail elsewhere herein. Such a strategy allows most of the complexity of device 300*c* to be prepared in solution. Gold nanoparticles 320*c*, 321*c* may directly contact, and directly bond to, electrodes 302*c*, 303*c* which also may be or include gold, and in this regard the nanoparticles may act as an extension of the electrodes themselves.

Devices such as illustrated herein may be made using any suitable operations. For example, FIG. 4 illustrates an example flow of operations in a method 400 for making the devices of FIG. 1, 2, or 3A-3D. Method 400 includes depositing a solution onto first and second electrodes separated from one another (operation 410). The solution may include particles in a liquid, each particle being coupled to a respective polymerase. For example, FIG. 5 schematically illustrates an example operation in the method of FIG. 4, in which a solution 570 including a plurality of particles 520 coupled to polymerases 505 is deposited onto first electrode 502 and second electrode 503, which may be supported by substrate 501. In one nonlimiting example, nanoparticle 320 illustrated in FIG. 3A includes reactive surface groups, e.g., streptavidin, and is bound to polymerase 305, e.g., via biotin-streptavidin binding. The nanoparticle-polymerase duplex 320, 305 is suspended in a suitable solution and deposited over electrodes 302, 303.

Method 400 illustrated in FIG. 4 includes transporting one of the particles from the solution to a space adjacent to the first and second electrodes (operation 420). For example, in the operation illustrated in FIG. 5, one of the particles 520 (with polymerase 105 attached thereto) is transported through solution 570 to the space adjacent to first electrode 502 and second electrode 503, e.g., to one or both of the space between and the space above first electrode 502 and second electrode 503. Such transport (indicated by large arrow) in some examples may be diffusion-based, e.g., may result from diffusional translational transport of the particle 520 through solution 570 using at least any suitable combination of gravity and Brownian motion. Additionally, or alternatively, such transport in some examples may include "passive" adsorption in which single particles are captured within or adjacent the space between electrodes, for example using at least surface interactions between the particles and electrodes. Such surface interactions may be maximized in such a conformation. Additionally, or alternatively, such transport may be driven by magnetic or dielectrophoretic trapping, which also may be referred to herein as "active" adsorption. In dielectrophoretic trapping, a direct current (DC) or alternating current (AC) electrical bias is applied across the electrodes to accelerate trapping of single particles within or adjacent to the space between those electrodes.

For example, in configurations in which particles 520 include tertiary polymer structures such as described with reference to FIG. 2, dielectrophoretic trapping may be used to accelerate transport of one of the particles to the space adjacent the electrodes. Or, for example, in configurations in which particles 520 include nanoparticles such as described with reference to FIGS. 3A-3D, dielectrophoretic trapping may be used to transport one of those particles to the space adjacent the electrodes.

Figure 13:
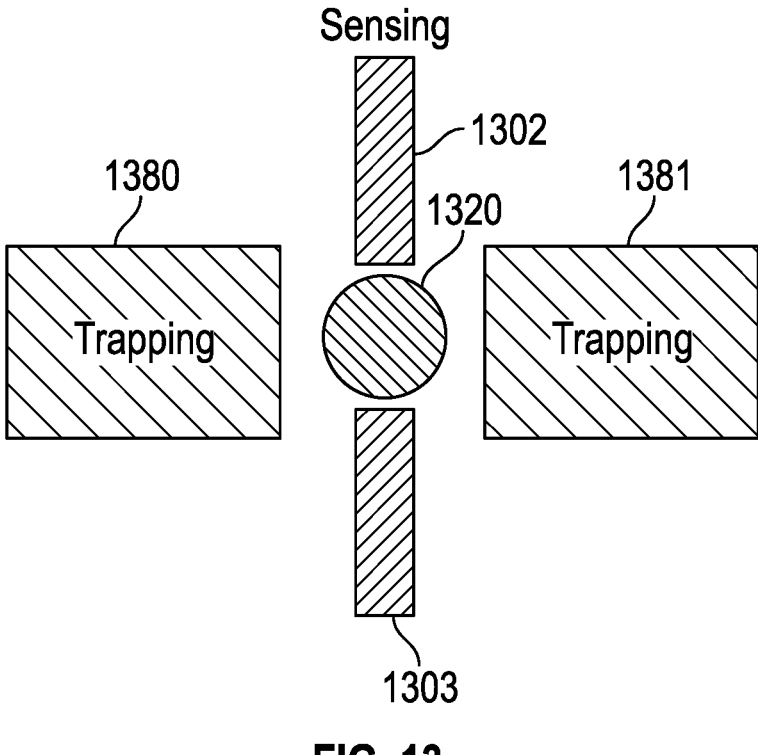
FIG. 13 schematically illustrates an example device to magnetically attract a particle.

In some examples of magnetic trapping, the particles may include a magnetic or ferromagnetic material and may be localized within respective device by applying a magnetic field. For example, FIG. 13 schematically illustrates an example device to magnetically attract a particle. Device 1300 includes first electrode 1302, second electrode 1303, particle 1320, first trapping electrode 1380, and second trapping electrode 1381. First electrode 1302 and second electrode 1303 may be configured similarly as first and second electrodes 102, 103 described with reference to FIGS. 1A-1B. Particle 1320 may include a magnetic or ferromagnetic material. First trapping electrode 1380 and second trapping electrode 1381 may be arranged orthogonally to first electrode 1302 and second electrode 1303, and may be coupled to control circuitry to apply a bias across such electrodes that is suitable to magnetically attract particle 1320 to the space between first trapping electrode 1380 and second trapping electrode 1381, and thus to the space between first electrode 1302 and second electrode 1303.

Referring again to FIG. 4, method 400 includes bonding the one of the particles to the first and second electrodes (operation 430). The bonding may include forming a first plurality of bonds between the first electrode and the one of the particles, and forming a second plurality of bonds between the second electrode and the one of the particles. Such bonding may result in formation of device 100 described with reference to FIG. 1A or device 100' described with reference to FIG. 1B, which may be exemplified as any of device 200 described with reference to FIG. 2, device 300 described with reference to FIG. 3A, device 300a described with reference to FIG. 3B, device 300b described with reference to FIG. 3C, or device 300c described with reference to FIG. 3D. The bonding may be direct, or may be indirect via intermediate structure(s) such as functional groups.

Note that during operations 420 and 430 of method 400 illustrated in FIG. 4, the particle being transported to space adjacent to the first and second electrodes may sterically exclude other particles from the space adjacent to the first and second electrodes. For example, as illustrated in FIG. 5, particle 520 may be sufficiently large relative to the space between first electrode 502 and second electrode 503 as to exclude other particles from the space adjacent to the first and second electrodes. For example, particle 520 may have a diameter that is about 10% or greater of the length L of the space between the electrodes. As such, there may be insufficient space for more than one of such particles in the space between or above those electrodes. Such exclusion alternatively may be referred to as geometric exclusion.

Figure 6A:
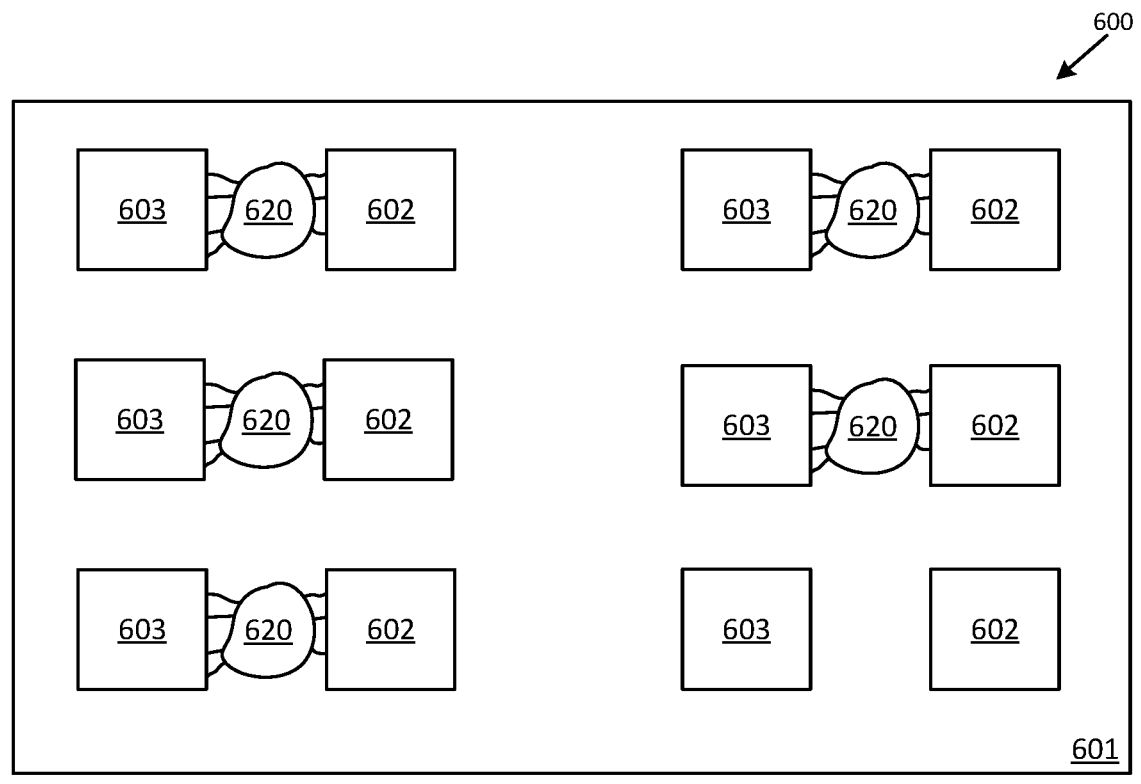
FIGS. 6A-6B schematically illustrate example device arrays including a plurality of the devices of FIG. 1, 2, or 3A-3D.
Figure 6B:
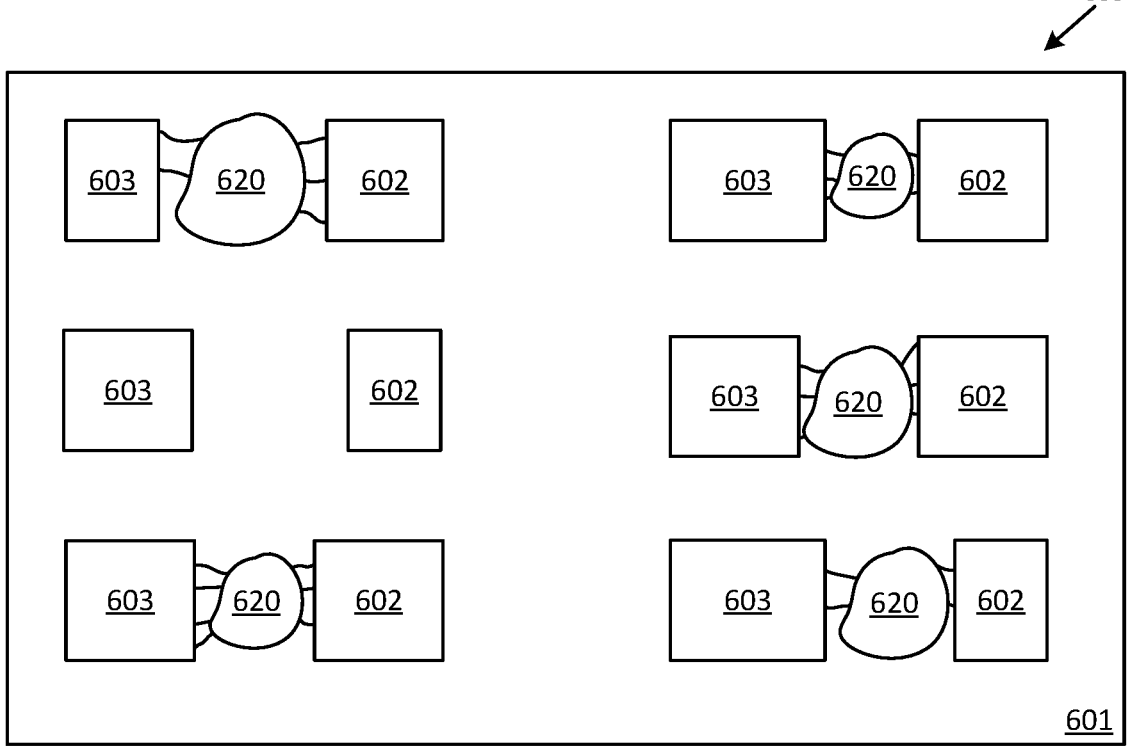

Using solution-based particle deposition methods such as described with reference to FIGS. 4-5 may provide for facile fabrication of multiple devices in parallel with one another. For example, FIGS. 6A-6B schematically illustrate example device arrays including a plurality of the devices of FIG. 1, 2, or 3A-3D. Array 600 illustrated in plan view in FIG. 6A includes a plurality of devices constructed similarly as device 100 described with reference to FIG. 1A or device 100' described with reference to FIG. 1B, which may be exemplified as any of device 200 described with reference to FIG. 2, device 300 described with reference to FIG. 3A, device 300a described with reference to FIG. 3B, device 300b described with reference to FIG. 3C, or device 300c described with reference to FIG. 3D. For example, devices of array 600 may include first electrode 602, second electrode 603, a single particle 620, and a polymerase coupled to the particle (polymerase not specifically shown in FIG. 6A), disposed on a common substrate 601. In this example, the spacing between electrodes 602 and 603 of each device may be substantially the same as one another, and particles 620 may have substantially the same size as one another and may be similarly bonded directly or indirectly to each of the electrodes via a plurality of bonds.

However, it should be appreciated that because of real-world processing variations, particles 620 may have a distribution of sizes. Additionally, or alternatively, because of real-world processing variations the size and spacing of electrodes 602, 603 may have distributions, particularly for smaller electrodes and smaller spacings. For example, for "nanoelectrodes" having spacings of about 100 nm or less, the spacing between electrodes of different electrode pairs may vary by about 10% or more, about 20% or more, or even about 30% or more, even within a common manufacturing process.

The present particle-based bridges may provide particular efficiencies for fabricating arrays which may have irregular electrode sizes and spacings and variations in particle sizes, such as illustrated in FIG. 6B. For example, array 600' illustrated in FIG. 6B includes some electrode pairs 602, 603 have relatively large spacing, some electrode pairs 602, 603 having relatively small spacing, and still other pairs 602, 603 having a spacing therebetween, disposed on a common substrate 601. Such variation in electrode size and spacing may, for example, result from manufacturing variations. Array 600' illustrated in FIG. 6B includes some particles 620 that are relatively large, some particles 620 that are relatively small, and some particles 620 having a size therebetween. Such variation in particle size may, for example, result from manufacturing variations. The variations in particle size and in the spacing between electrodes may synergistically allow for fabrication of an array in which devices include exactly one particle. For example, larger particles may sterically exclude other particles from electrode pairs with larger spacings, but such particles may themselves be sterically excluded, because of their size, from electrode pairs with smaller spacings. Smaller particles may sterically exclude other particles from electrode pairs with smaller spacings, and may be sterically excluded from electrode pairs with larger spacings using other, larger particles. In comparison, if all of the particles were the same size, then depending on how great the variations in electrode spacing were there might be some electrode pairs that were too small to accommodate the particles, or which are large enough that steric exclusion does not apply and thus potentially allowing multiple particles between the electrodes.

Figure 7:
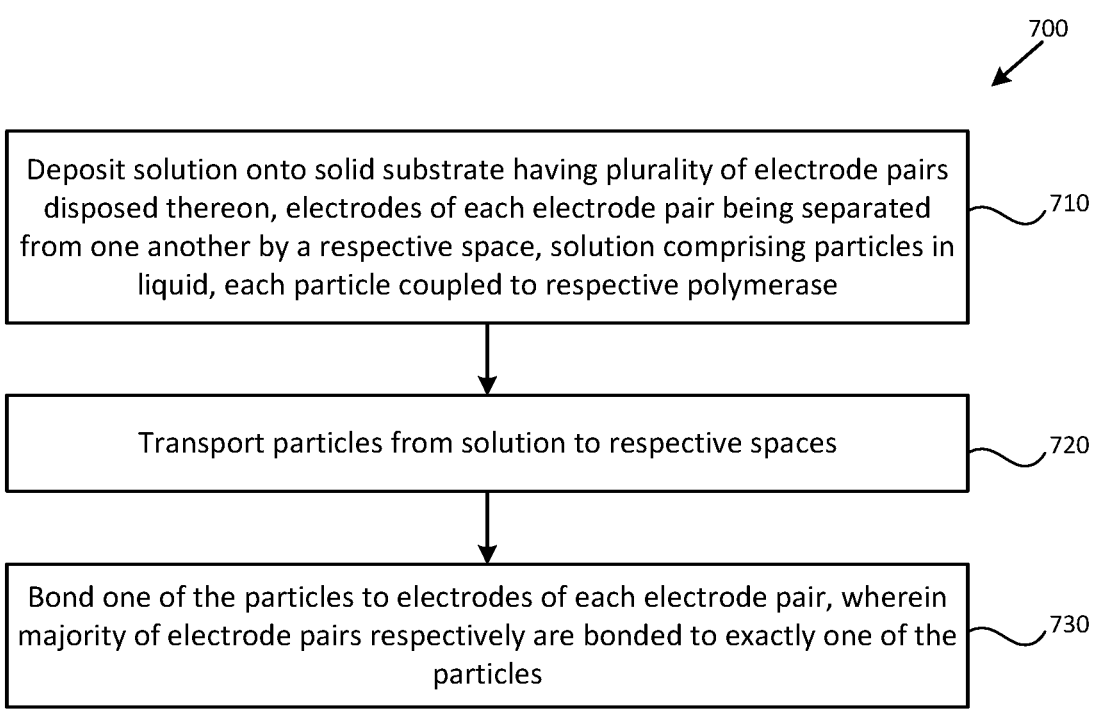
FIG. 7 illustrates an example flow of operations in a method for making the device array of FIGS. 6A-6B.

FIG. 7 illustrates an example flow of operations in a method 700 for making the device arrays of FIGS. 6A-6B. Method 700 includes depositing a solution onto a substrate having a plurality of electrode pairs disposed thereon (operation 710). The electrodes of each electrode pair may be separated from one another by a respective space. The solution may include particles in liquid, each particle being coupled to a respective polymerase. Note that, because the solution applied during operation 710 includes particles that are already coupled to polymerases, that solution may be subjected to quality control—for example, to confirm appropriate coupling between the particles and the polymerases, and to confirm activity of the polymerases, and to take any remedial action as may be appropriate—before the particles are bonded to the electrodes. As such, the solution may have a relatively high yield of functional polymerases which are correctly coupled to respective particles, and as such the devices of the array may be prepared in relatively high yield. In other examples, the particles instead are bonded to the electrodes before coupling the polymerase to the particle.

Method 700 illustrated in FIG. 7 includes transporting one of the particles from the solution to a space adjacent to the first and second electrodes (operation 720). Operation 720 may include methods of transport such as described with reference to FIGS. 4-5, e.g., may include any suitable combination of one or more of diffusion-based transport, passive adsorption, dielectrophoretic trapping, and magnetic trapping.

Referring again to FIG. 7, method 700 includes bonding the one of the particles to the electrodes of each electrode pair, wherein a majority of the electrode pairs respectively are bonded to exactly one of the particles (operation 730). The bonding may include forming a first plurality of bonds between the first electrode of that pair and the one of the particles, and forming a second plurality of bonds between the second electrode of that pair and the one of the particles in a manner similar to that described with reference to operation 430 of FIG. 4. The bonding may be direct or indirect via intermediate structure(s) such as functional groups. Such bonding may result in formation of an array of devices 100 described with reference to FIG. 1A or of devices 100' described with reference to FIG. 1B, which may be exemplified as any of device 200 described with reference to FIG. 2, device 300 described with reference to FIG. 3A, device 300a described with reference to FIG. 3B, device 300b described with reference to FIG. 3C, or device 300c described with reference to FIG. 3D. Similarly as described with reference to operations 420 and 430 of method 400 illustrated in FIG. 4, during method 700 the particles respectively being transported to the spaces adjacent to the electrode pairs may sterically exclude other particles from the space adjacent to the electrodes of that pair. As described with reference to FIGS. 6A-6B, even if there are variations in spacing between electrodes of electrode pairs, the present particles respectively may synergistically be transported to—and sterically exclude other particles from—electrode pairs of appropriate spacing for those particles.

In comparison, in the limit where there is no steric exclusion or another way to inhibit more than one particle from bonding to an electrode pair, devices of the array may include multiple bridges between the electrodes of respective devices, and may include different numbers of bridges between the electrodes of respective devices. In such a limit, the distribution of bridges per device may follow a Poisson distribution. Such a distribution of device construction may result in poor yield of usable devices, e.g., may cause variations in electrical conductivity resulting from differences between bridges rather than from labels that are coupled to nucleotides being added to a sequence. In this regard, the present particles may provide a sub-Poisson distribution of device fabrication, e.g., may provide a majority of devices that have exactly one particle bonded to each electrode pair, for example, greater than about 50%—e.g., greater than about 60%, greater than about 70%, greater than about 80%, greater than about 90%, greater than about 95%, or even about 100%, of devices that have exactly one particle bonded to each electrode pair. Even if occasionally a device is fabricated that is missing a particle, as suggested in the arrays illustrated FIGS. 6A-6B, the yield of usable devices using at least the present particles may be expected to be significantly higher than for devices for which the Poisson distribution governs fabrication.

The present devices may be used for any suitable purpose. Although examples provided below describe use of the present devices for sequencing polynucleotides, it should be appreciated that the devices are not so limited.

Figure 8A:
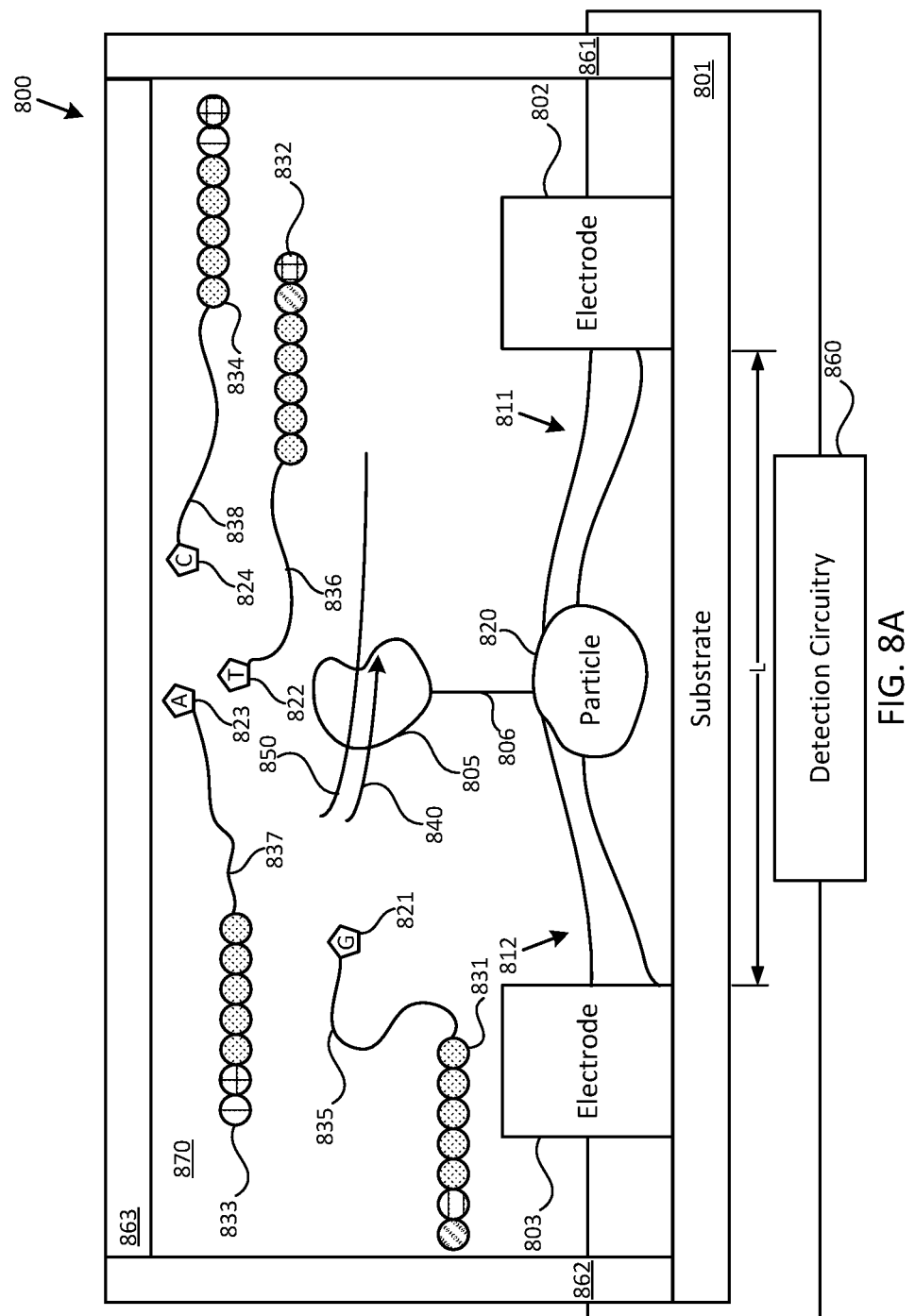
FIGS. 8A-8B schematically illustrate an example composition for sequencing a polynucleotide that includes a particle-based bridge between electrodes.
Figure 8B:
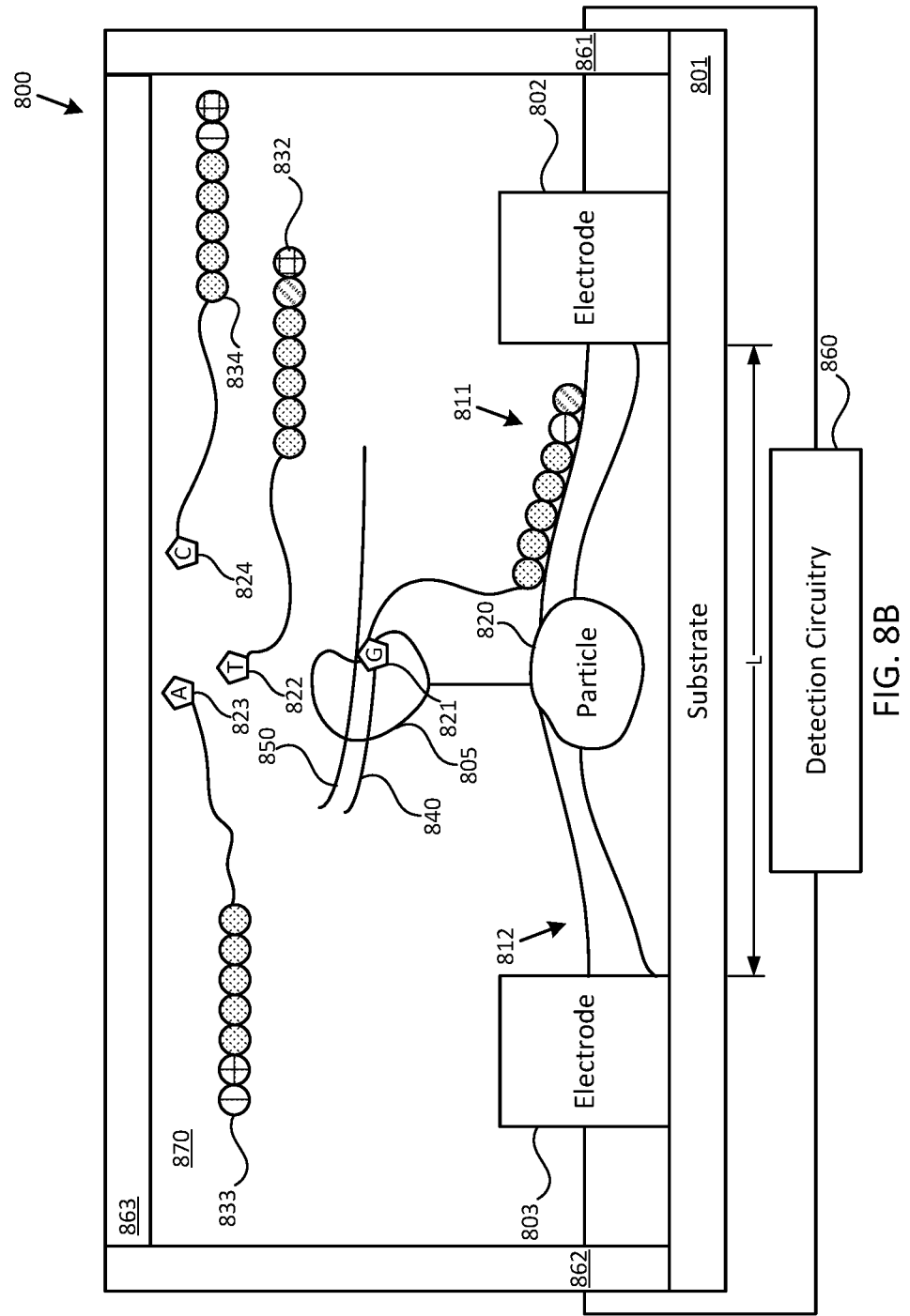

FIGS. 8A-8B schematically illustrate an example composition for sequencing a polynucleotide that includes a particle-based bridge between electrodes. Referring now to FIG. 8A, composition 800 includes substrate 801, first electrode 802, second electrode 803, polymerase 804, particle 820, nucleotides 821, 822, 823, and 824, labels 831, 832, 833, and 834 respectively coupled to those nucleotides, first polynucleotide 840, second polynucleotide 850, and detection circuitry 860. Polymerase 805 in some examples may be coupled to particle 820 via linker 806 in a manner such as known in the art. In the example illustrated in FIGS. 8A-8B, components of composition 800 may be enclosed within a flow cell (e.g., having walls 861, 862, 862) filled with fluid 820 in which nucleotides 821, 822, 823, and 824 (with associated labels), polynucleotides 840, 850, and suitable reagents may be carried.

Substrate 801 may support first electrode 802 and second electrode 803. First electrode 802 and second electrode 803 may be separated from one another by a space, e.g., a space of length L as indicated in FIG. 8A, which may have dimensions such as described with reference to FIGS. 1A-1B. Particle 820 may be bonded to first electrode 802 via a first plurality of bonds including functional groups 811 and may be bonded to second electrode 803 via a second plurality of bonds including functional groups 812 so as to form a bridge spanning the space between first electrode 802 and second electrode 803. Nonlimiting example configurations for particle 820, electrodes 802, 803, and bonds including functional groups 811, 812 are provided elsewhere herein, e.g., with reference to FIGS. 1A-1B, 2, and 3A-3D.

As explained in greater detail below with reference to FIG. 8B, in this example labels 831, 832, 833, and 834 respectively may hybridize to one or more of functional groups 811, 812 in such a manner as to modulate the electrical conductivity between electrodes 802, 803, based upon which modulation the identity of the corresponding nucleotides 821, 822, 823, and 824 may be determined. For example, particle 820 and functional groups 811, 812 may form at least part of an electrically conductive bridge between the first and second electrodes 802, 803, and labels 831, 832, 833, and 834 may alter the current between the first and second electrodes by hybridizing to one or more of the functional groups. In another example, the particle includes a pair of nanoparticles coupled to one another by a linker in a manner such as described with reference to FIG. 3D, and labels 831, 832, 833, and 834 may alter the current between the first and second electrodes by hybridizing to the linker.

For example, composition 800 illustrated in FIG. 8A may include any suitable number of nucleotides coupled to corresponding labels, e.g., one or more nucleotides, two or more nucleotides, three or more nucleotides, four nucleotides, or five or more nucleotides. For example, nucleotide 821 (illustratively, G) may be coupled to corresponding label 831, in some examples via linker 835. Nucleotide 822 (illustratively, T) may be coupled to corresponding label 832, in some examples via linker 836. Nucleotide 823 (illustratively, A) may be coupled to corresponding label 833, in some examples via linker 836. Nucleotide 824 (illustratively, C) may be coupled to corresponding label 834, in some examples via linker 837. The couplings between nucleotides and labels, in some examples via linkers which may include the same or different polymer as the labels, may be provided using any suitable methods known in the art. Labels 831, 832, 833, and 834 may include the same type of polymer as one another, but may differ from one another in at least one respect, e.g., may have different sequences of monomer units than one another. In some examples, labels 831, 832, 833, and 834 in some examples may include the same type of polymer as in functional groups 811, 812. In a manner such as described in greater detail with reference to FIG. 8B, the sequences of the monomer units within the respective labels 831, 832, 833, and 834 may be respectively selected so as to facilitate generation of distinguishable electrical currents through particle 820 when those labels hybridize with one or more of functional groups 811, 812.

Composition 800 illustrated in FIG. 8A includes first polynucleotide 840 and second polynucleotide 850, and polymerase 805 to add nucleotides of the plurality of nucleotides 821, 822, 823, and 824 to first polynucleotide 840 using at least a sequence of second polynucleotide 850. The labels 831, 832, 833, and 834 corresponding to those nucleotides respectively may hybridize to one or more of functional groups 811, 812 in a manner such as described in greater detail below with reference to FIG. 8B. Detection circuitry 860 is to detect a sequence in which polymerase 805 respectively adds the nucleotides 821, 822, 823, and 824 (not necessarily in that order) to first polynucleotide 840 using at least changes in a current through particle 820, the changes being responsive to the hybridizations between the one or more functional groups 811 and the labels 831, 832, 833, and 834 corresponding to those nucleotides. For example, detection circuitry 860 may apply a voltage across first electrode 802 and second electrode 803, and may detect any current that flows through particle 820 responsive to such voltage, for example, through the use of a transamped-ance amplified circuit. At the particular time illustrated in FIG. 8A, none of labels 831, 832, 833, and 834 are hybridized to any of functional groups 811, 812, and so a relatively low current (or no current) may flow through particle 820. Although nucleotides 821, 822, 823, 824 may diffuse freely through fluid 820 and respective labels 831, 832, 833, 834 may briefly hybridize to one or more of functional groups 811, 812 as a result of such diffusion, the labels may rapidly dehybridize and so any resulting changes to the electrical conductivity of particle 820 are expected to be so short as either to be undetectable, or as to be clearly identifiable as not corresponding to addition of a nucleotide to first poly-nucleotide 840.

In comparison, FIG. 8B illustrates a time at which poly-merase 805 is adding nucleotide 821 (illustratively, G) to first polynucleotide 840 using at least the sequence of second polynucleotide 850 (e.g., so as to be complementary to a C in that sequence). Because polymerase 805 is acting upon nucleotide 821 to which label 831 is attached (in some examples via linker 837), such action maintains label 831 at a location that is sufficiently close to at least one of func-tional groups 811 for a sufficient amount of time to maintain hybridization with that functional group 811 to cause a sufficiently long change in the electrical conductivity of particle 820 as to be detectable using detection circuitry 860, allowing identification of nucleotide 821 as being added to first polynucleotide 840. For example, label 831 may have a property that, when hybridized to a functional group 811, imparts the bridge with an electrical conductivity via which detection circuitry 860 may uniquely identify the added nucleotide as 821 (illustratively G) as compared to one of the other nucleotides. Similarly, label 832 may have a property that, when hybridized to a functional group 811, imparts the bridge with an electrical conductivity via which detection circuitry 860 may uniquely identify the added nucleotide as 822 (illustratively T) as compared to one of the other nucleotides. Similarly, label 833 may have a property that, when hybridized to a functional group 811, imparts the bridge with an electrical conductivity via which detection circuitry 860 may uniquely identify the added nucleotide as 823 (illustratively C) as compared to one of the other nucleotides. Similarly, label 834 may have a property that, when hybridized to a functional group 811, imparts the bridge with an electrical conductivity via which detection circuitry 860 may uniquely identify the added nucleotide as 824 (illustratively C) as compared to one of the other nucleotides.

In one nonlimiting example, labels 831, 832, 833, 834 include respective oligonucleotides having at least partially different sequences than one another, and at least one functional group 811 includes a polynucleotide (e.g., as described with reference to FIGS. 3B-3D) which in some examples has the same length as those oligonucleotides, such that hybridization of the labels to that functional group 811 provides a fully double-stranded polynucleotide along the length of particle 820. The label's respective oligonucle-otide sequences may hybridize differently with the sequence of the polynucleotide of that functional group 811. For example, one or more monomers within label 831 may be nucleotides that are the same as or different from one another. The first and second signal monomers of the other labels may be nucleotides that are different in sequence or in type, or both, from the corresponding monomers of the other labels, such that each label 831, 832, 833, 834 has a unique sequence of corresponding monomers. The respective hybridization between those monomers for each label and the polynucleotide of that functional group 811 may provide a particular electrical current through particle 820. For example, label 831 may have a sequence with a particular pair of bases that hybridizes so as to modulate the electrical conductivity of the bridge to a first level; label 832 may have a sequence with a particular pair of bases that hybridizes so as to modulate the electrical conductivity of the bridge to a second level that is different from the first level; label 833 may have a sequence with a particular pair of bases that hybridizes so as to modulate the electrical conductivity of the bridge to a third level that is different from the first and second levels; and label 834 may have a sequence with a particular pair of bases that hybridizes so as to modulate the electrical conductivity of the bridge to a fourth level that is different from the first, second, and levels.

It will be appreciated that the functional group 811 to which the labels hybridize may include any suitable combination, order, and type of monomer units (e.g., nucleotides) to allow currents resulting from different labels to be detected and distinguished from one another. Similarly, the labels 831, 832, 833, and 834 respectively may include any suitable combination, order, and type of monomer units (e.g., nucleotides) to allow currents from different labels to be detected and distinguished from one another. In some examples, one or more other functional groups 811, 812 (and in some examples, all other functional groups 811, 812) may have different combinations, orders, and types of monomer units selected to inhibit hybridization to the labels, so that the labels do not hybridize to such other functional groups 811, 812.

Figure 9A:
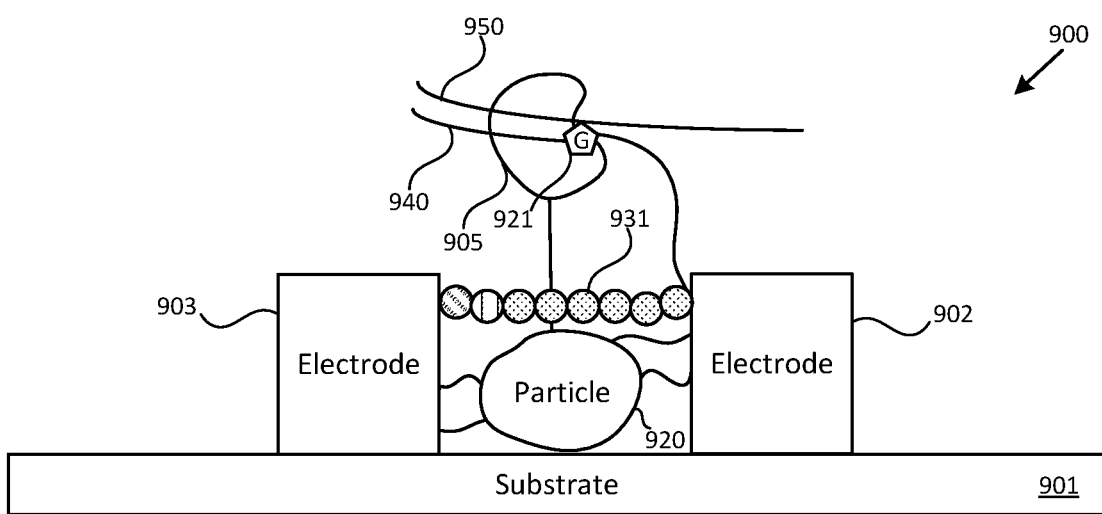
FIGS. 9A-9B schematically illustrate other example compositions for sequencing a polynucleotide that include a particle-based bridge between electrodes.
Figure 9B:
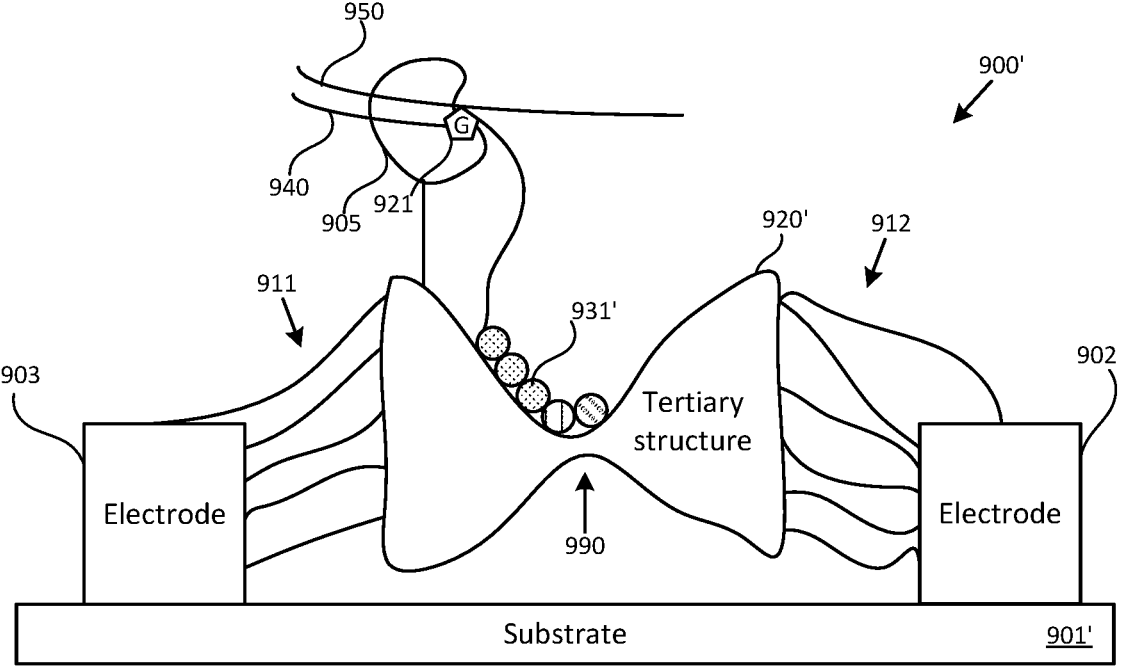

The components included within the bridge between the electrodes and within the labels coupled to the nucleotides may include any suitable material(s) such as exemplified herein. In certain examples such as described with reference to FIGS. 8A-8B, these materials may include polymers, such as polynucleotides. FIGS. 9A-9B schematically illustrate other example compositions for sequencing a polynucleotide that includes a particle-based bridge between electrodes. FIG. 9A schematically illustrates an example composition 900 for sequencing a polynucleotide that includes an electrically nonconductive particle-based bridge. In the example shown in FIG. 9A, composition 900 may be configured similarly as composition 800 described with reference to FIGS. 8A-8B, e.g., includes first electrode 902, second electrode 903, polymerase 905, and particle 920 bonded directly to first electrode 902 via a first plurality of bonds 911, or indirectly via functional groups, and bonded directly to second electrode 903 via a second plurality of bonds 912, or indirectly via functional groups. Polymerase 905 may be coupled to particle 920 via a linker, and may add nucleotides such as nucleotide 921 to first polynucleotide 940 using at least the sequence of second polynucleotide 950. Composition 900 may include other components such as described with reference to FIGS. 8A-8B, omitted here.

In the example illustrated in FIG. 9A, particle 920 may be electrically nonconductive, such that particle 920 and bonds 911, 912 do not provide a pathway for electrical current between first electrode 902 and second electrode 903. Label 931 coupled to nucleotide 921 may form a transient electrically conductive bridge between first and second electrodes 902, 903 via which the current flows. The other labels of other nucleotides (not specifically shown) similarly may form transient electrically conductive bridges that provide respective currents between that are distinguishable from one another in a manner similar to that described with reference to FIGS. 8A-8B. For example, one or more of the labels (and in some examples all of the labels, independently from one another) may be selected from the group consisting of carbon dots, electrically conductive polymers, pi-conjugated small molecules, nanotubes, fullerenes, and inorganic nanoparticles. In some examples, the labels may be longer than the length of the space between the electrodes.

FIG. 9B schematically illustrates an example composition 900' for sequencing a polynucleotide that includes a tertiary polymer structure-based bridge. In the example shown in FIG. 9B, composition 900' may be configured similarly as composition 800 described with reference to FIGS. 8A-8B, e.g., includes first electrode 902, second electrode 903, polymerase 905, and nucleotide 921 coupled to oligonucleotide label 931'. Tertiary polymer structure 920' may be configured in a manner such as described with reference to FIG. 2, e.g., may include a polynucleotide (such as DNA) or a polypeptide. Tertiary polymer structure 920' may be bonded directly to first electrode 902 via a first plurality of bonds 911, or indirectly via functional groups, and bonded directly to second electrode 903 via a second plurality of bonds 912, or indirectly via functional groups. Polymerase 905 may be coupled to tertiary polymer structure 920' via a linker, and may add nucleotides such as nucleotide 921 to first polynucleotide 940 using at least the sequence of second polynucleotide 950. Composition 900' may include other components such as described with reference to FIGS. 8A-8B, omitted here.

In the example illustrated in FIG. 9B, tertiary polymer structure 920' may be electrically conductive, such that tertiary polymer structure 920' and bonds 911, 912 (in some examples including functional groups) form an electrically conductive bridge between first electrode 902 and second electrode 903. Label 931' of nucleotide 921 may alter the current between first and second electrodes 902, 903 by hybridizing to a portion of tertiary polymer structure 920'. The other labels of other nucleotides (not specifically shown) similarly may hybridize to a portion of tertiary polymer structure 920' to provide respective currents between that are distinguishable from one another in a manner similar to that described with reference to FIGS. 8A-8B.

Compositions such as described with reference to FIGS. 8A-8B and FIGS. 9A-9B may be used in any suitable method for sequencing a polynucleotide. For example, FIG. 10 illustrates an example flow of operations in a method 1000 for sequencing a polynucleotide any of the compositions of FIG. 8A-8B or 9A-9B. Method 1000 illustrated in FIG. 10 includes adding, using a polymerase, nucleotides to a first polynucleotide using at least a sequence of a second polynucleotide (operation 1010). For example, polymerase 805 described with reference to FIGS. 8A-8B may add each of nucleotides 821, 822, 823, and 824 to first polynucleotide 840 using at least the sequence of second polynucleotide 850. Or, for example, polymerase 905 described with reference to FIGS. 9A-9B may add nucleotide 921 and other nucleotides to a first polynucleotide using at least the sequence of a second polynucleotide (other nucleotides and first and second polynucleotides not specifically shown).

Method 1000 illustrated in FIG. 10 may include changing, using labels respectively coupled to the nucleotides, a current between first and second electrodes (operation 1020). A particle may be coupled to the first electrode via a first plurality of bonds and may be coupled to the second electrode via a second plurality of bonds. Such bonds may be direct or indirect (e.g., may include functional groups). For example, labels 831, 832, 833, 834 described with reference to FIGS. 8A-8B respectively may be coupled to nucleotides 821, 822, 823, and 824. As polymerase 805 respectively adds those nucleotides to first polynucleotide 840, the labels coupled to those nucleotides respectively may hybridize to a functional group 811 so as to change electrical conduction between first electrode 802 and second electrode 803. Or, for example, label 931 described with reference to FIG. 9A may be coupled to nucleotide 921, and other labels may be coupled to other nucleotides (other labels and other nucleotides not specifically shown). As polymerase 905 respectively adds those nucleotides to the first polynucleotide, the labels coupled to those nucleotides respectively may form transient electrically conductive bridges between first electrode 902 and second electrode 903. Or, for example, label 931' described with reference to FIG. 9B may be coupled to nucleotide 921, and other labels may be coupled to other nucleotides (other labels and other nucleotides not specifically shown). As polymerase 905 respectively adds those nucleotides to first polynucleotide 940, the labels coupled to those nucleotides respectively may hybridize to a portion of the tertiary polymer structure, thus changing the current between first electrode 902 and second electrode 903.

Referring again to FIG. 10, method 1000 may include detecting a sequence in which the polymerase adds the nucleotides to the first polynucleotide using at least changes in current through the bridge caused using the labels corresponding to those nucleotides (operation 1030). For example, detection circuitry 860 described with reference to FIGS. 8A-8B may detect changes in current through the bridge responsive to respective hybridizations between labels 831, 832, 833, and 834 and functional groups 811. Similar detection circuitry (not specifically illustrated) may detect changes in current resulting from formation of transient electrically conductive bridges using label 931 (and other similar labels), such as illustrated in FIG. 9A. Similar detection circuitry (not specifically illustrated) may detect changes in current through tertiary polymer structure 920', illustrated in FIG. 9B, responsive to respective hybridizations between label 931' (and other similar labels) and a portion of tertiary polymer structure 920'.

In another nonlimiting example, nanoparticle 320 illustrated in FIG. 3A includes reactive surface groups, e.g., streptavidin, and is bound to polymerase 305, e.g., via biotin-streptavidin binding. Nucleotide reagents may be modified to include respective conductivity labels that are capable of changing the electrical conductivity (or electrical resistance) between electrodes 302, 303 when the labels are in close proximity to the space between those electrodes. Detection circuitry may perform base calling (nucleotide detection) using at least observing electrical signals as a first polynucleotide is extended using at least the sequence of a second polynucleotide, where nucleotides coupled to distinguishable electrical conductivity labels produce distinguishable transient changes in electrical conductivity during the nucleotide incorporation event.

In another nonlimiting example, nanoparticle 320a illustrated in FIG. 3B may be coupled to DNA duplexes 311a, 312b bonding the nanoparticle to first electrode 302a and second electrode 303a and providing an electrically conductive path from one electrode to the other via the DNA duplexes. Sensing of analytes (such as labels coupled to nucleotides) may be achieved via any suitable mode of molecular interaction between the analytes and the nanoparticle 320a having DNA duplexes 311a, 312b coupled thereto, e.g., via hydrogen bonding, hybridization, intercalation, groove binding, or the like.

In another nonlimiting example, gold nanoparticles 320c, 321c and DNA linker 330c illustrated in FIG. 3D form a dumbbell shaped complex providing nanoparticle-molecular junction device 300c, in which the nanoparticles may act as an extension of the electrodes themselves. The DNA duplex linker, by its single-molecule nature, may be highly sensitive to any mode of intermolecular interaction with analytes (such as labels coupled to nucleotides), e.g., via hydrogen bonding, hybridization, intercalation, groove binding, or the like.

Figure 14:
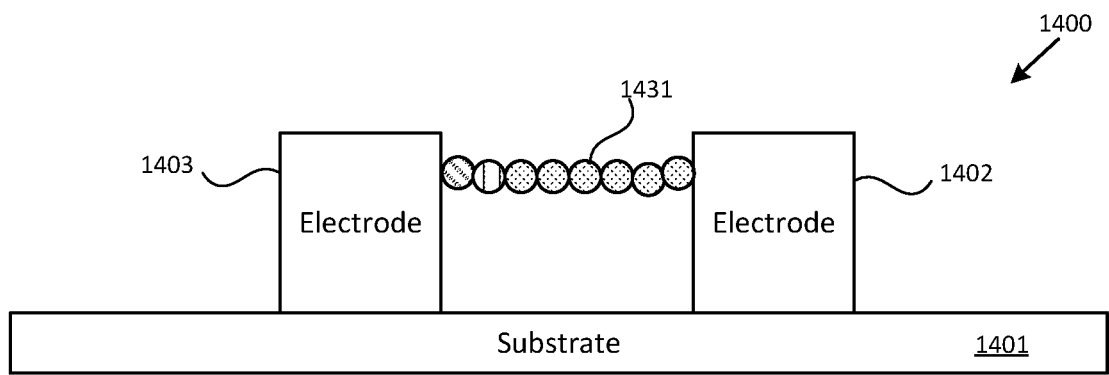
FIG. 14 schematically illustrates an example composition including a transient bridge between electrodes.

Components of compositions such as described with reference to FIGS. 9A-9B are not limited to use in sequencing polynucleotides, and indeed are not limited to use with particles or polymerases. For example, FIG. 14 schematically illustrates an example composition 1400 including a transient bridge between electrodes. Composition 1400 includes first electrode 1402 and second electrode 1403 separated from one another by a space; a fluid including a first electrically conductive label 1431 having a length at least as long as a length of the space; and detection circuitry (not specifically illustrated in FIG. 14) to generate a first signal responsive to transient formation, using the first electrically conductive label, of a first electrically conductive bridge between the first and second electrodes. Illustratively, the fluid may include electrically conductive label 1431 which may be configured similarly as electrically conductive label 931 described with reference to FIG. 9A, e.g., a label which has a length at least as long as a length of the space between first electrode 1402 and second electrode 1403, but which need not necessarily be coupled to a nucleotide. Detection circuitry configured similarly to detection circuitry 860 may generate a signal responding to transient formation, using electrically conductive label 1431, of an electrically conductive bridge between first and second electrodes 1402, 1403. In some examples, electrically conductive label 1431 may transiently bond to each of the first and second electrodes 1402, 1403 to form the first electrically conductive bridge. The fluid may include any suitable number of electrically conductive labels, e.g., at least a second electrically conductive label (not specifically illustrated), having a length at least as long as a length of the space, and the detection circuitry may generate a second signal responsive to transient formation, using the second electrically conductive label, of a second electrically conductive bridge between the first and second electrodes 1402, 1403. The detection circuitry further may distinguish between formation of the first electrically conductive bridge and the second electrically conductive bridge using at least a difference between the first signal and the second signal, e.g., in a manner similar to how detection circuitry 860 may distinguish between different labels.

In some examples, electrically conductive label 1431 includes a first reactive group to transiently bond to first electrode 1402, and a second reactive group to transiently bond to second electrode 1403. In some nonlimiting examples, the first and second reactive groups may be selected from the group consisting of: thiols, amines, isothiocyanides, phosphines, carboxyls, selenos, pyridines, and methylsulfides. The detection circuitry further may apply a bias voltage across the first electrically conductive bridge that disrupts the transient bond between the first reactive group and the first electrode and the transient bond between the second reactive group and the second electrode. For examples of molecules that may transiently bond to electrodes via such reactive groups, which transient bond may be disrupted using application of an appropriate bias voltage, see the following reference, the entire contents of which are incorporated by reference herein: Li et al., "Electric field breakdown in single molecule junctions," J. Am. Chem. Soc. 137(15): 5028-5033 (2015). Example molecules such as described in Li may be used as labels in a manner such as described herein. A useful feature of such examples is that after the bonding of the label to the electrodes is disrupted, current between the electrodes is disrupted and the electrodes are immediately ready to accept transient bonds with another such label. Additionally, the amount of time with which respective labels are transiently bonded to the electrodes may be controlled using at least the timing of applying the bias voltage to disrupt the transient bonds.

In some examples, each electrically conductive label 1431 includes one respective type of reactive group that may be disrupted above a specific threshold voltage. In some nonlimiting examples, the reactive group may be selected from the group consisting of: thiols, amines, isothiocyanides, phosphines, carboxyls, selenos, pyridines, and methylsulfides. The label identity may be encoded in the electrical conductivity of the transient bridge. For example, the transient bridges may include different polymer sequences than one another which may provide different conductivities between the electrodes based upon which the respective labels may be identified. This electrical conductivity may be set or tuned by altering the physical or chemical properties of the label. In such examples, because each type of label may include the same type of reactive group as one another, preparation and implementation may be simplified relative to providing different reactive groups for each type of label.

Figure 15:
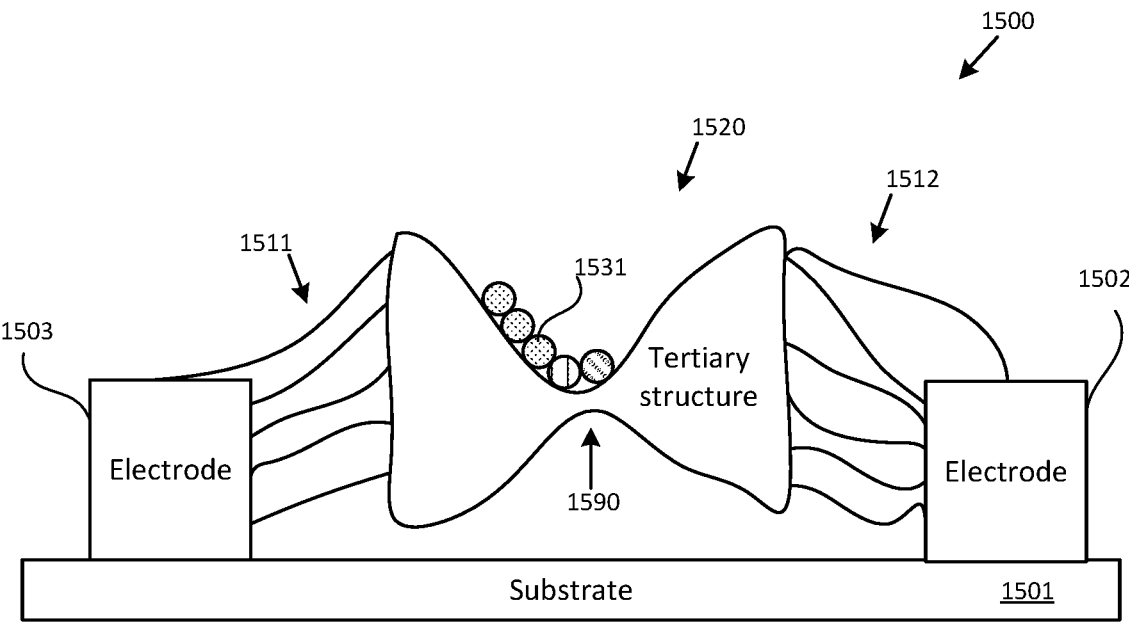
FIG. 15 schematically illustrates an example composition including a transient bridge between electrodes.

FIG. 15 schematically illustrates an example composition 1500 including a transient bridge between electrodes. Composition 1500 is not limited to use in sequencing polynucleotides, and indeed is not limited to use with particles or polymerases, but in some examples can be used for sequencing polynucleotides in a manner similar to composition 900' described with reference to FIG. 9B. Composition 1500 includes first electrode 1502 and second electrode 1503 separated from one another by a space, and a bridge 1520 spanning the space between the first and second electrodes. Bridge 1520 may include a polymer chain (such as a polynucleotide) or other suitable structure, which in some examples may be provided in a tertiary structure including construction 1590 such as illustrated in FIG. 15 or may be provided in a functional group such as illustrated in FIGS. 3B-3D. Electrically conductive label 1531 may transiently bond to bridge 1520 in such a manner as to provide an electrically conductive bridge between the first and second electrodes 1502, 1503 based upon which the label identity may be determined. In one nonlimiting example, the labels (e.g., label 1531) may include an oligonucleotide. For example, suitable detection circuitry may generate a signal responsive to formation of the electrically conductive bridge. The detection circuitry further may apply a bias voltage across the resulting electrically conductive bridge that disrupts the transient bond between the label 1531 and bridge 1520 following generation of the signal. The rate at which labels 1531 transiently bond to bridge 1520 may be referred to as an on rate. Following such transient bonding, labels 1531 may be left in place for a desired amount of time, e.g., after sufficient data has been collected for a high-confidence base call, thus resulting in a selected and controlled off rate upon applying the removal bias voltage. The label identity may be encoded in electrical conductivity differences between respective labels 1531, or using rupture characteristics of the labels (e.g., a voltage or time at which the labels respectively dissociate from the bridge responsive to the applied bias voltage). In some examples, the polymer chains of bridge 1520 and labels each include polynucleotides such as DNA, RNA, PNA, or the like. In one nonlimiting example, the polymer chain of the bridge includes ssDNA, at least one of the labels includes ssDNA that hybridizes to the bridge to provide A-form dsDNA, and at least one of the labels includes ssDNA that hybridizes to the bridge to provide B-form dsDNA. The resulting A-form dsDNA and B-form dsDNA may have different conductivities than one another based upon which the resulting nucleotides may be identified. Application of a bias voltage may cause the labels to disassociate, e.g., based upon the respective hybridizations between the labels and the polymer chains of the bridge being less stable than the bridge itself.

Figure 16A:
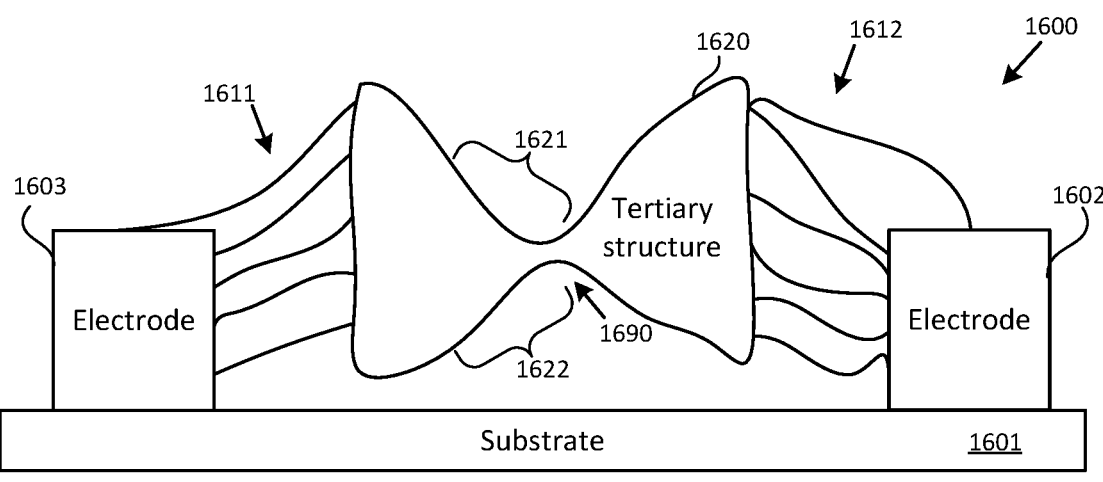
FIGS. 16A-16C schematically illustrate an example composition with bridges that may be selectively completed.
Figure 16B:
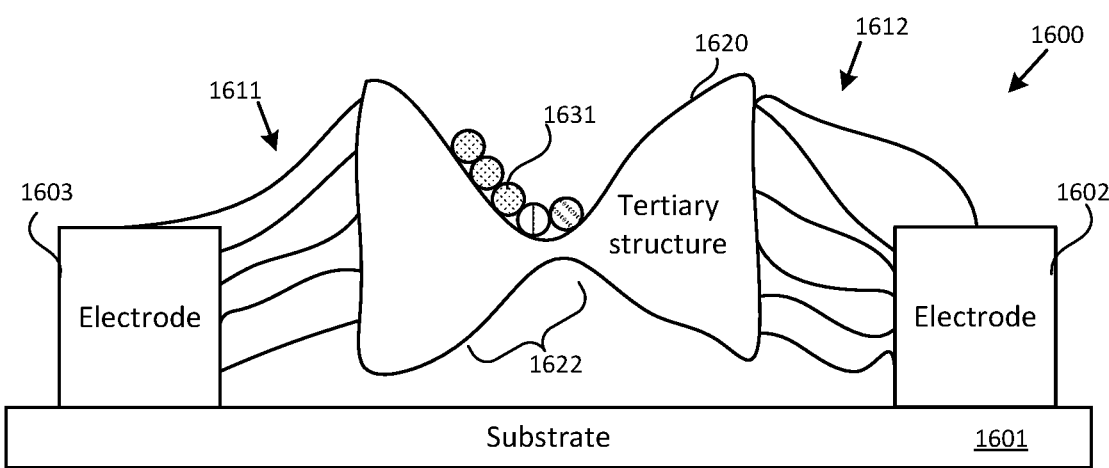
Figure 16C:
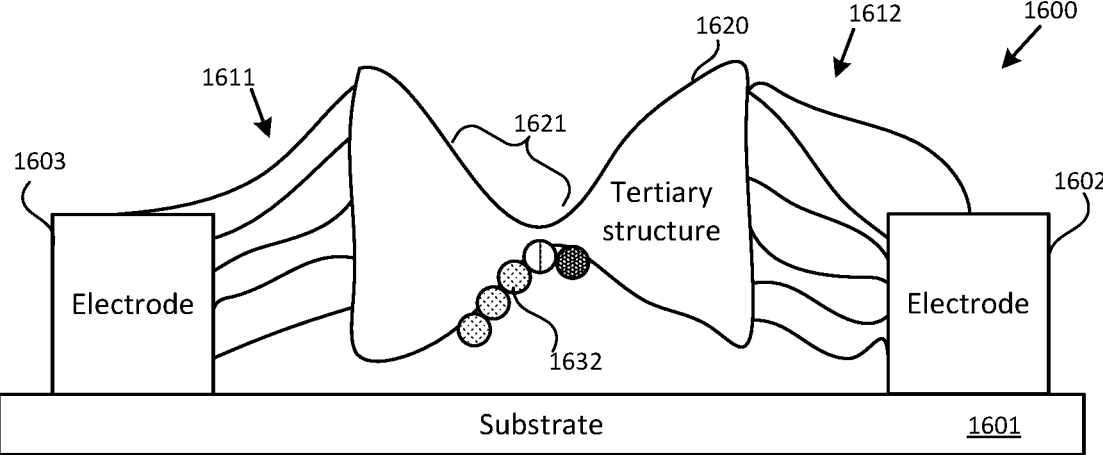

FIGS. 16A-16C schematically illustrate an example composition 1600 with bridges that may be selectively completed. Composition 1600 is not limited to use in sequencing polynucleotides, and indeed is not limited to use with particles or polymerases, but in some examples can be used for sequencing polynucleotides in a manner similar to composition 900' described with reference to FIG. 9B. Composition 1600 includes first electrode 1602 and second electrode 1603 separated from one another by a space, and first and second bridges spanning the space between the first and second electrodes. The first bridge may include a first polymer chain, and the second bridge may include a second polymer chain that is different from the first polymer chain. For example, in the nonlimiting configuration illustrated in FIGS. 16A-16C, tertiary polymer structure 1620 such as described with reference to FIG. 2 or FIG. 9B may include a single polymer molecule that is folded multiple times and cross-linked so as to form distinguishable polymer chains 1621, 1622 each of which corresponds to a bridge that may be selectively completed. For example, a fluid may include first oligomer 1631 that hybridizes to first polymer chain 1621 and not to second polymer chain 1622. For example, first oligomer 1631 may be configured similarly as label 831 described with reference to FIG. 8A but need not necessarily be coupled to a nucleotide, and may have a sequence based upon which oligomer 1631 will hybridize to first polymer chain 1621 and not to second polymer chain 1622 in a manner such as illustrated in FIG. 16B. Detection circuitry similar to detection circuitry 860 may generate a first signal responsive to hybridization of first oligomer 1631 to the first polymer chain.

The fluid may include any suitable number of oligomers that respectively are to hybridize with any suitable polymer chain or chains of tertiary polymer 1620 structure. Illustratively, the fluid further may include second oligomer 1632 that may hybridize to second polymer chain 1622 and not to first polymer chain 1631 in a manner such as illustrated in FIG. 16C, and the detection circuitry may generate a second signal responsive to hybridization of second oligomer 1632 to the second polymer chain. In a manner similar to that described elsewhere herein, the detection circuitry further may distinguish between hybridization of first oligomer 1631 with first polymer chain 1621 and hybridization of second oligomer 1632 with second polymer chain 1622 using at least a difference between the first signal and the second signal, e.g., using at least different sequences of the first and second polymer chains 1621, 1622 or using at least different sequences of the first and second oligomers 1631, 1632. In this regard, first and second oligomers 1631, 1632 may be considered to selectively complete bridges within tertiary polymer structure 1620. Similarly, the fluid may include third and fourth oligomers may selectively hybridize with third and fourth polymer chains of tertiary structure 1620 so as to provide different electrical conductivities between electrodes 1602, 1603. Examples of tertiary structures include polynucleotide tertiary structures (e.g., DNA origami) or polypeptide tertiary structures such as described with reference to FIGS. 2 and 9B. For example, first and second polymer chains 1621, 1622 (and any additional polymer chains, if provided) in some examples may include respective single stranded DNA sequences, and first and second oligonucleotides 1631, 1632 (and any additional oligonucleotides, if provided) respectively include single stranded DNA sequences that respectively complement and selectively hybridize to one of the single stranded DNA sequences. In some examples, each of the polymer chains (e.g., 1621, 1622) may span at least a portion of constriction 1690. First and second oligonucleotides 1631, 1632 in some examples may be removed by applying a bias voltage in a manner such as described with reference to FIG. 15.

Accordingly, the devices, compositions, and methods described herein may provide for enhanced control of the fabrication of electronic devices with relatively few components. The present devices, compositions, and methods may be used with any suitable particles, which in some examples may include functional groups. Such functional groups may include, for example, polynucleotides (such as DNA), small organic molecules, polymers, or π-conjugated materials. Another example feature of the present devices, compositions, and methods may include the ability to accommodate variability in the spaces between electrodes, because particles of different sizes may be easily be prepared and may therefore be tailored for different sized spaces. For example, a single solution of nanoparticles with a distribution of sizes may be used to self-select an appropriately sized particle for each respective device in an array, and therefore may accommodate variability in the spaces between electrodes within that array, e.g., in a manner such as described with reference to FIGS. 6A-6B and 7. Another example feature of the present devices, compositions, and methods may include ease of quality control, because the respective assemblies of particles, polymerases, and electrodes readily may be imaged using standard microscopy techniques such as scanning electron microscopy (SEM), atomic force microscopy (AFM), and the like.

Non-Limiting Working Examples

The following examples are purely illustrative, and not intended to be limiting.

Figure 11A:
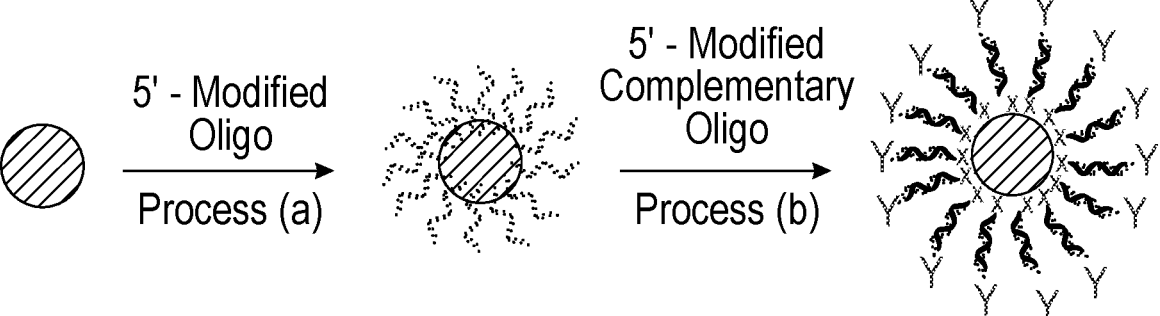
FIG. 11A illustrates an example flow of operations in a method for preparing a device such as illustrated in FIG. 3B.
Figure 11B:
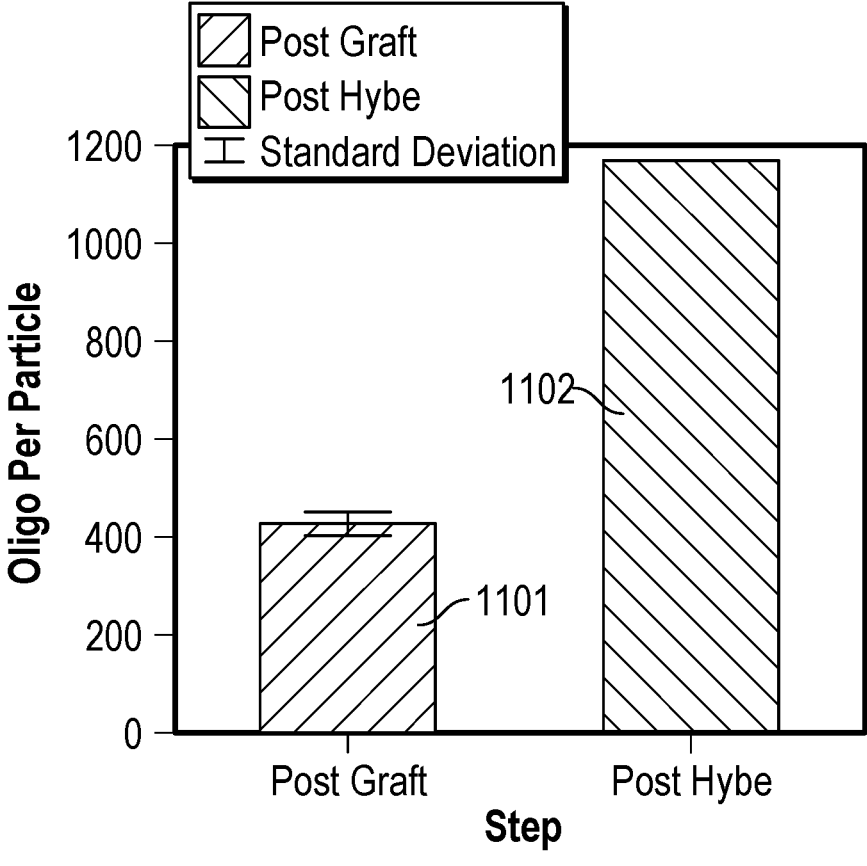
FIG. 11B illustrates example results of the operations illustrated in FIG. 11A.

FIG. 11A illustrates an example flow of operations in a method for preparing a device such as illustrated in FIG. 3B. In the nonlimiting example illustrated in FIG. 11A, at process (a), an approximately 20 nm gold nanoparticle was reacted with a thiol group at the terminal end of a 5'-modified 30-mer oligonucleotide (10 nm long nominally). At process (b), the 5'-modified oligonucleotide then was hybridized with a 5'-modified complimentary 30-mer oligonucleotide having a disulfide group at its outward-facing terminal end, thus providing a gold nanoparticle surrounded by a DNA duplex with a reactive disulfide corona (indicated by "Y" groups in FIG. 11A). FIG. 11B illustrates example results of the method illustrated in FIG. 11A. More specifically, in FIG. 11B, a fluorescence assay characterization of the number of oligonucleotides per particle after grafting single-stranded oligonucleotides to the nanoparticles (1101)

and after hybridizing those single-stranded oligonucleotides to the complementary oligonucleotides (1102) are shown.

Figure 11D:
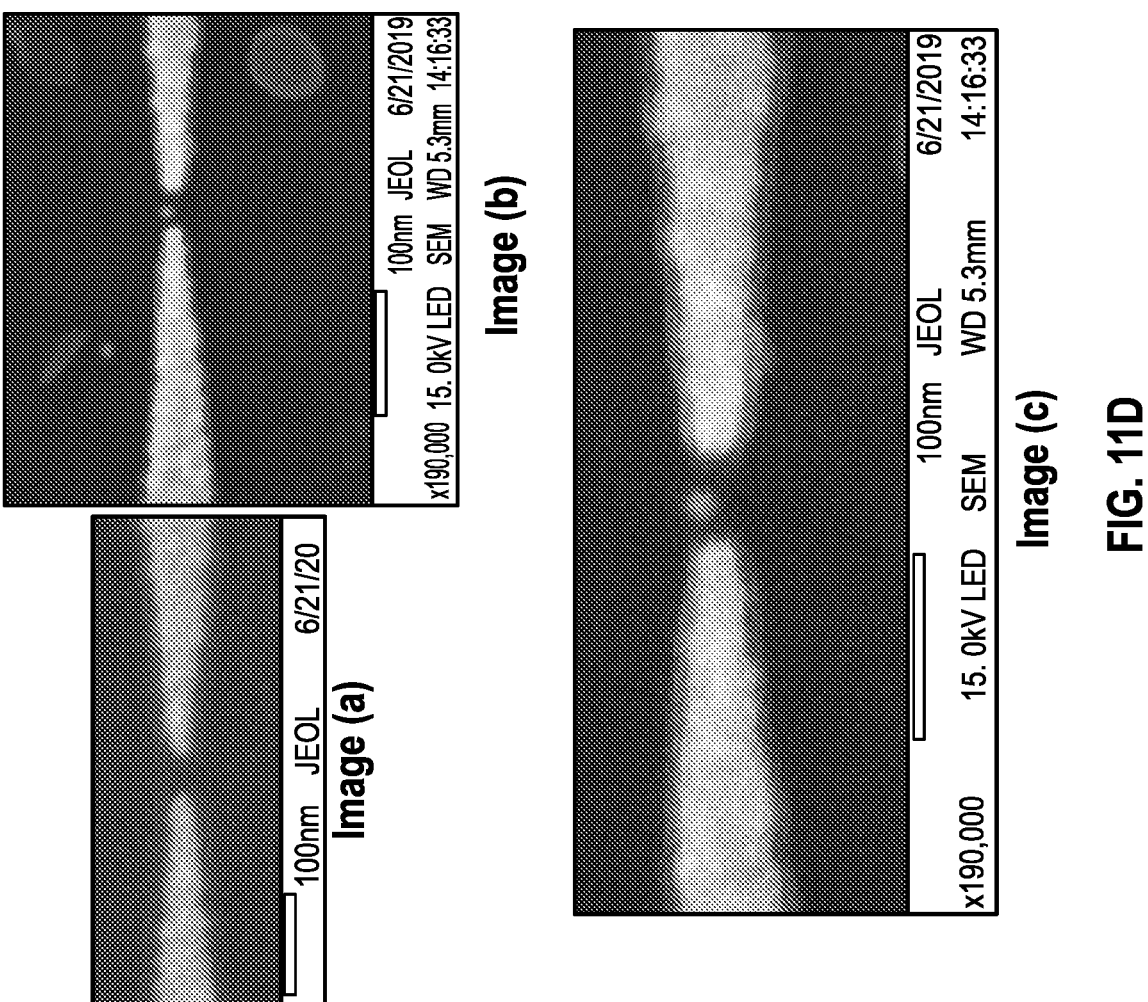
FIG. 11D illustrates example results of the operations illustrated in FIG. 11C.

FIG. 11C illustrates an example flow of additional operations in a method for preparing a device such as illustrated in FIG. 3B. Operations (a) and (b) described with reference to FIG. 11A were used to prepare gold nanoparticles surrounded by a DNA duplex with a reactive disulfide corona (indicated by "DS" groups in FIG. 11C), and those prepared gold nanoparticles then were coupled to electrodes. More specifically, at process (c) the functionalized nanoparticles were dissolved in a liquid, and the liquid applied to a pair of gold electrodes that were spaced apart from one another by about 50-60 nm. A single particle in the liquid was transported to the gold electrodes and was bonded to the electrodes. FIG. 11D illustrates example results of the operations illustrated in FIG. 11C. Image (a) of FIG. 11D is an SEM image of the bare gold electrodes prior to process (c) of FIG. 11C. The electrodes may be seen to be spaced apart from one another by less than 100 nm, here approximately 30 nm. Image (b) of FIG. 11D is an SEM image of the gold electrodes following process (c) of FIG. 11C, in which it may be seen that a single gold nanoparticle is disposed between the gold electrodes. Image (c) of FIG. 11D is a zoomed-in SEM image of the single gold nanoparticle disposed between the gold electrodes. It may be understood from image (c) of FIG. 11D that the gold nanoparticle has a diameter that is smaller than the spacing between the electrodes, and that the nanoparticle is spaced apart approximately evenly from each of the electrodes. This approach produced single nanoparticle devices in a yield of approximately 5-10%. Higher yields may be expected by actively trapping single particles using an AC or DC electric field applied by respective electrode pairs.

Figure 12A:
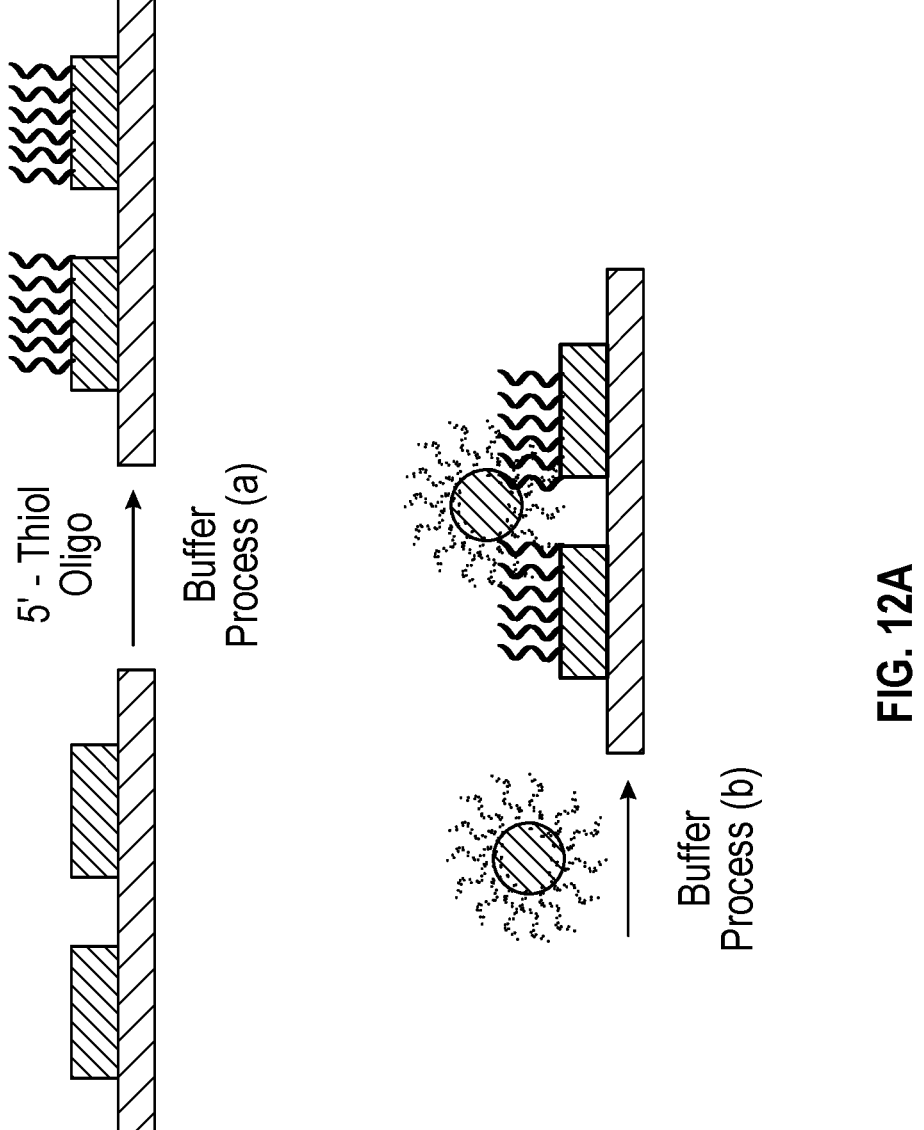
FIG. 12A illustrates an example flow of operations in a method for preparing a device such as illustrated in FIG. 3C.
Figure 12B:
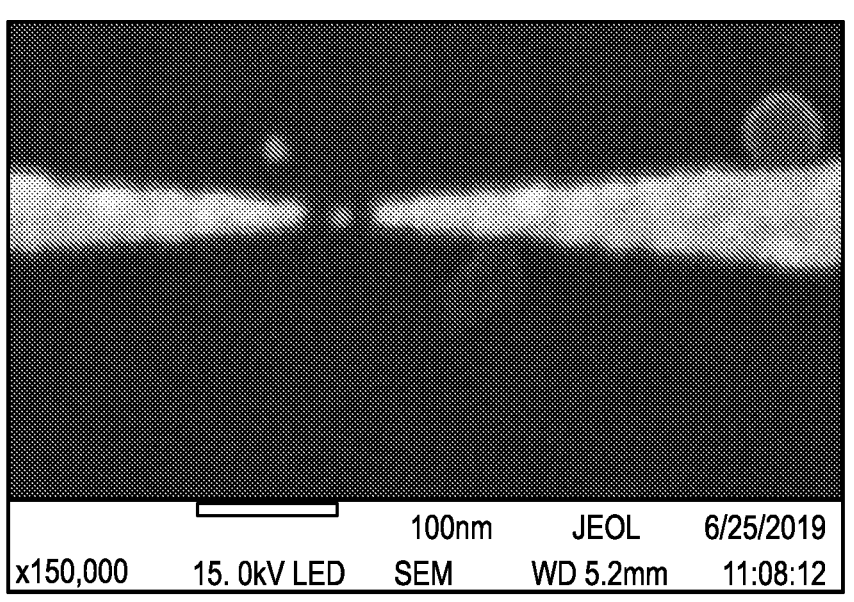
FIG. 12B illustrates example results of the operations illustrated in FIG. 12A.

FIG. 12A illustrates an example flow of operations in a method for preparing a device such as illustrated in FIG. 3C. In the nonlimiting example illustrated in FIG. 12A, at process (a), bare gold electrodes similar to those described with reference to FIGS. 11A-11D were reacted with a thiol group at the terminal end of a 5'-modified 30-mer oligonucleotide, in a buffer solution. At process (b), the 5'-modified oligonucleotide then was hybridized with a 5'-modified complimentary 30-mer oligonucleotide which was attached to an approximately 20 nm gold nanoparticle which had been produced using process (a) of FIG. 11A. The result was a gold nanoparticle surrounded by single stranded DNA that formed duplexes with single stranded DNA coupled to gold electrodes spaced apart from one another by about 50-60 nm. FIG. 12B illustrates example results of the operations illustrated in FIG. 12A. More specifically, FIG. 12B is an SEM image of the gold electrodes following process (b) of FIG. 12A, in which it may be seen that a single gold nanoparticle is disposed between the gold electrodes. This approach produced single nanoparticle devices in a yield of approximately 5-10%. Higher yields may be expected by actively trapping single particles using an AC or DC electric field applied by respective electrode pairs.

While various illustrative examples are described above, it will be apparent to one skilled in the art that various changes and modifications may be made therein without departing from the invention. The appended claims are intended to cover all such changes and modifications that fall within the true spirit and scope of the invention.

What is claimed is:
1. A device comprising:
a first electrode;
a second electrode separated from the first electrode by a gap;

a particle coupled to the first electrode via a first plurality of bonds, each bond of the first plurality of bonds disposed between the particle and the first electrode, and coupled to the second electrode via a second plurality of bonds, each bond of the second plurality of bonds disposed between the particle and the second electrode;

a polymerase coupled to the particle;

a bridge defined by the particle, the first plurality of bonds and the second plurality of bonds disposed between the first electrode and the second electrode and having an electrical conductivity; wherein the particle, or one or more bonds of the first plurality of bonds, or one or more bonds of the second plurality of bonds comprises a functional group configured to transiently alter the electrical conductivity of the bridge by transiently interacting with a label.

2. The device of claim 1, wherein the particle is electrically nonconductive.

3. The device of claim 1, wherein the particle comprises a polymer having a tertiary structure.

4. The device of claim 3, wherein the polymer comprises a polynucleotide or a polypeptide.

5. The device of claim 4, wherein the polynucleotide or the polypeptide is folded and cross-linked into the tertiary structure, the tertiary structure having a central constriction within the bridge.

6. The device of claim 1, wherein the particle comprises a nanoparticle with the functional group bonding the nanoparticle to one of the first and second electrodes.

7. The device of claim 6, wherein the nanoparticle is inorganic.

8. The device of claim 1, wherein the gap has a length and the particle has a diameter of at least about 10% of the length of the gap.

9. The device of claim 1, wherein the particle comprises a first nanoparticle coupled to a second nanoparticle via a linker.

10. The device of claim 1, wherein the label comprises an oligonucleotide, a DNA intercalator, or a DNA groove binding agent.

11. A method of making the device of claim 1, the method comprising:

depositing a solution onto the first electrode and the second electrode, the solution comprising the particle coupled to the polymerase in a liquid;

transporting the particle from the solution to a space adjacent to the first electrode and the second electrode; and forming the first plurality of bonds and the second plurality of bonds by bonding the particle to each of the first and second electrodes.

12. The method of claim 11, wherein the transporting comprises dielectrophoretically or magnetically trapping the particle to the first electrode and to the second electrode.

13. The method of claim 11, further comprising sterically excluding, using the particle, other particles from the space adjacent to the first and second electrodes.

14. The method of claim 11, wherein the particle is electrically nonconductive.

15. The method of claim 11, wherein the particle comprises a polymer having a tertiary structure.

16. The method of claim 15, wherein the polymer comprises a polynucleotide or a polypeptide.

17. The method of claim 16, comprising folding and cross-linking the polynucleotide or the polypeptide into the tertiary structure, the tertiary structure having a central constriction, the central constriction forming part of the bridge.

18. The method of claim 11, wherein the particle comprises a nanoparticle with a functional group bonding the nanoparticle to the first electrode or to the second electrode.

19. The method of claim 18, wherein the nanoparticle is inorganic.

20. The method of claim 11, wherein the gap has a length and the particle has a diameter of at least about 10% of the length of the gap.

21. A device array comprising:

two or more of the device of claim 1 disposed on a solid substrate.

22. A composition comprising:

the device of claim 1;

a first polynucleotide and second a second polynucleotide;

a plurality of nucleotides, each nucleotide being coupled to a corresponding label of a plurality of labels; wherein the polymerase is configured to add the nucleotides to the first polynucleotide using at least a sequence of the second polynucleotide; and detection circuitry configured to detect a sequence of addition of the nucleotides to the first polynucleotide based on current variations between the first electrode and the second electrode wherein the current variations are in response to the labels corresponding to the added nucleotides.

23. A method of sequencing nucleic acid using the composition of claim 19, the method comprising:

adding, using a polymerase, nucleotides to the first polynucleotide using at least partially a sequence of the second polynucleotide;

transiently changing, using labels respectively coupled to the plurality of nucleotides, a current through a bridge between the first electrode and the second electrode; and detecting a sequence in which the polymerase adds the nucleotides to the first polynucleotide based on current variations through the bridge in response to transient bonding between the labels corresponding to the added nucleotides and the functional group.

* * * * *